(12) United States Patent
Amans et al.

(10) Patent No.: US 9,315,487 B2
(45) Date of Patent: Apr. 19, 2016

(54) TETRAHYDROQUINOLINE DERIVATIVES USEFUL AS BROMODOMAIN INHIBITORS

(75) Inventors: Dominique Amans, Stevenage (GB); Emmanuel Hubert Demont, Stevenage (GB); Katherine Louise Jones, Stevenage (GB); Jonathan Thomas Seal, Stevenage (GB); Ann Louise Walker, Stevenage (GB)

(73) Assignee: GlaxoSmithKline LLC, Philadelphia, PA (US)

( * ) Notice: Subject to any disclaimer, the term of this patent is extended or adjusted under 35 U.S.C. 154(b) by 0 days.

(21) Appl. No.: 14/114,545

(22) PCT Filed: May 2, 2012

(86) PCT No.: PCT/EP2012/057978
§ 371 (c)(1),
(2), (4) Date: Oct. 29, 2013

(87) PCT Pub. No.: WO2012/150234
PCT Pub. Date: Nov. 8, 2012

(65) Prior Publication Data
US 2014/0066459 A1  Mar. 6, 2014

(30) Foreign Application Priority Data
May 4, 2011 (GB) .................... 1107325.1

(51) Int. Cl.
| | | |
|---|---|---|
| *A61K 31/4706* | (2006.01) | |
| *C07D 401/04* | (2006.01) | |
| *C07D 401/10* | (2006.01) | |
| *A61K 31/497* | (2006.01) | |
| *A61K 45/06* | (2006.01) | |
| *C07D 401/14* | (2006.01) | |

(52) U.S. Cl.
CPC .......... *C07D 401/04* (2013.01); *A61K 31/4706* (2013.01); *A61K 31/497* (2013.01); *A61K 45/06* (2013.01); *C07D 401/10* (2013.01); *C07D 401/14* (2013.01)

(58) Field of Classification Search
CPC .......................... A61K 31/4706; C07D 401/14
See application file for complete search history.

(56) References Cited

FOREIGN PATENT DOCUMENTS

| EP | 1435356 A1 | 7/2004 |
|---|---|---|
| WO | 2006/083692 A2 | 8/2006 |
| WO | 2011/054841 A1 | 5/2011 |
| WO | 2011/054848 A1 | 5/2011 |
| WO | 2012/143413 A1 | 10/2012 |
| WO | 2012/143415 A1 | 10/2012 |

*Primary Examiner* — Wu-Cheng Winston Shen
*Assistant Examiner* — Christopher R Stone
(74) *Attorney, Agent, or Firm* — Robert H. Brink

(57) ABSTRACT

Tetrahydroquinoline compounds pharmaceutical compositions containing such compounds and their use in therapy.

8 Claims, No Drawings

TETRAHYDROQUINOLINE DERIVATIVES USEFUL AS BROMODOMAIN INHIBITORS

CROSS-REFERENCE TO RELATED APPLICATIONS

This application is filed pursuant to 35 USC 371 as a United States National Phase Application of International Patent Application Serial No. PCT/EP2012/057978 filed on May 2, 2012, which claims priority from 1107325.1 filed on May 4, 2011 in the United Kingdom.

FIELD OF THE INVENTION

The present invention relates to compounds, pharmaceutical compositions containing such compounds and to their use in therapy.

BACKGROUND OF THE INVENTION

The genomes of eukaryotic organisms are highly organised within the nucleus of the cell. The long strands of duplex DNA are wrapped around an octomer of histone proteins (most usually comprising two copies of histones H2A, H2B H3 and H4) to form a nucleosome. This basic unit is then further compressed by the aggregation and folding of nucleosomes to form a highly condensed chromatin structure. A range of different states of condensation are possible, and the tightness of this structure varies during the cell cycle, being most compact during the process of cell division. Chromatin structure plays a critical role in regulating gene transcription, which cannot occur efficiently from highly condensed chromatin. The chromatin structure is controlled by a series of post translational modifications to histone proteins, notably histones H3 and H4, and most commonly within the histone tails which extend beyond the core nucleosome structure. These modifications include acetylation, methylation, phosphorylation, ubiquitinylation, SUMOylation. These epigenetic marks are written and erased by specific enzymes, which place the tags on specific residues within the histone tail, thereby forming an epigenetic code, which is then interpreted by the cell to allow gene specific regulation of chromatin structure and thereby transcription.

Histone acetylation is most usually associated with the activation of gene transcription, as the modification loosens the interaction of the DNA and the histone octomer by changing the electrostatics. In addition to this physical change, specific proteins bind to acetylated lysine residues within histones to read the epigenetic code. Bromodomains are small (~110 amino acid) distinct domains within proteins that bind to acetylated lysine resides commonly but not exclusively in the context of histones. There is a family of around 50 proteins known to contain bromodomains, and they have a range of functions within the cell.

The BET family of bromodomain containing proteins comprises 4 proteins (BRD2, BRD3, BRD4 and BRD-t) which contain tandem bromodomains capable of binding to two acetylated lysine residues in close proximity, increasing the specificity of the interaction. BRD2 and BRD3 are reported to associate with histones along actively transcribed genes and may be involved in facilitating transcriptional elongation (Leroy et al, Mol. Cell. 2008 30(1):51-60), while BRD4 appears to be involved in the recruitment of the pTEF-β complex to inducible genes, resulting in phosphorylation of RNA polymerase and increased transcriptional output (Hargreaves et al, Cell, 2009 138(1): 129-145). It has also been reported that BRD4 or BRD3 may fuse with NUT (nuclear protein in testis) forming novel fusion oncogenes, BRD4-NUT or BRD3-NUT, in a highly malignant form of epithelial neoplasia (French et al. Cancer Research, 2003, 63, 304-307 and French et al. Journal of Clinical Oncology, 2004, 22 (20), 4135-4139). Data suggests that BRD-NUT fusion proteins contribute to carcinogenesis (Oncogene, 2008, 27, 2237-2242). BRD-t is uniquely expressed in the testes and ovary. All family members have been reported to have some function in controlling or executing aspects of the cell cycle, and have been shown to remain in complex with chromosomes during cell division—suggesting a role in the maintenance of epigenetic memory. In addition some viruses make use of these proteins to tether their genomes to the host cell chromatin, as part of the process of viral replication (You et al Cell, 2004 117(3):349-60).

Japanese patent application JP2008-156311 discloses a benzimidazole derivative which is said to be a BRD2 bromodomain binding agent which has utility with respect to virus infection/proliferation.

Patent application WO2009084693A1 discloses a series of thienotriazolodiazepiene derivatives that are said to inhibit the binding between an acetylated histone and a bromodomain containing protein which are said to be useful as anti-cancer agents.

Patent applications PCT/EP2010/06693 (published as WO2011054841) and PCT/EP2010/066701 (published as WO2011054848) both disclose a series of tetrahydroquinoline derivatives that inhibit the binding of BET family bromodomains with acetylated lysine residues.

A class of compounds have been found which inhibit the binding of bromodomains with its cognate acetylated proteins, more particularly a class of compounds that inhibit the binding of BET family bromodomains to acetylated lysine residues. Such compounds will hereafter be referred to as "bromodomain inhibitors".

SUMMARY OF THE INVENTION

In a first aspect of the present invention, there is provided a compound of formula (I) or a salt thereof, more particularly a compound of formula (I) or a pharmaceutically acceptable salt thereof

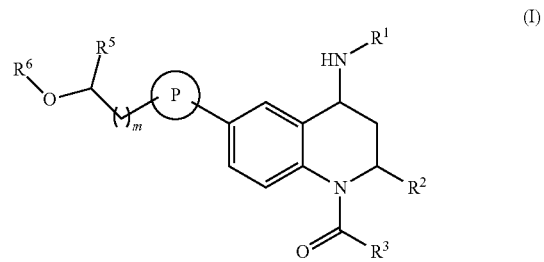

In a second aspect of the present invention, there is provided a pharmaceutical composition comprising a compound of formula (I) or a pharmaceutically acceptable salt thereof and one or more pharmaceutically acceptable carriers, diluents or excipients.

In a third aspect of the present invention, there is provided a compound of formula (I), or a pharmaceutically acceptable salt thereof for use in therapy, in particular in the treatment of diseases or conditions for which a bromodomain inhibitor is indicated.

In a fourth aspect of the present invention, there is provided a method of treating diseases or conditions for which a bromodomain inhibitor is indicated in a subject in need thereof which comprises administering a therapeutically effective amount of a compound of formula (I) or a pharmaceutically acceptable salt thereof.

In a fifth aspect of the present invention, there is provided the use of a compound of formula (I), or a pharmaceutically acceptable salt thereof in the manufacture of a medicament for the treatment of diseases or conditions for which a bromodomain inhibitor is indicated.

DETAILED DESCRIPTION OF THE INVENTION

The present invention relates to compounds of formula (I) or a salt thereof

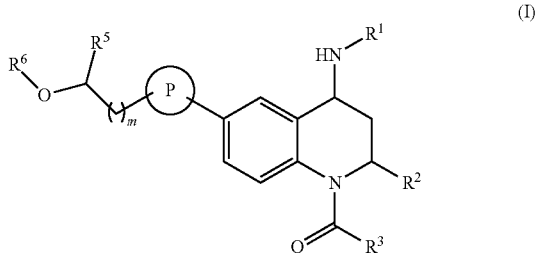

in which
P is pyrazolyl or triazolyl;
$R^1$ is a group $C(O)OR^4$ in which $R^4$ is $C_{1-3}$alkyl or $C_{3-7}$cycloalkyl; or
$R^1$ is a group selected from phenyl, pyridyl, pyrazinyl and pyrimidinyl said groups being optionally substituted by one or two substituents selected from halogen, $C_{1-4}$alkyl and CN;
$R^2$ is $C_{1-4}$alkyl;
$R^3$ is $C_{1-4}$alkyl;
$R^5$ is H or $C_{1-4}$alkyl;
$R^6$ is $C_{1-4}$alkyl;
or $R^5$ and $R^6$, together with the O to which $R^6$ is attached, form an oxetanyl, tetrahydrofuranyl or tetrahydropyranyl ring;
m is 1 or 2.

In one embodiment the invention provides compounds of formula (I) with cis relative stereochemistry across the tetrahydroquinoline ring in respect of the substituents in the 2 and 4 position on the ring. In one embodiment the compound of formula (I) or a salt thereof is the (2S,4R) enantiomer.

In one embodiment P is a group

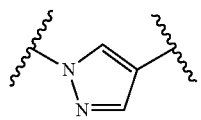 [SMILES: *c1cnn(*)c1]

In one embodiment P is selected from

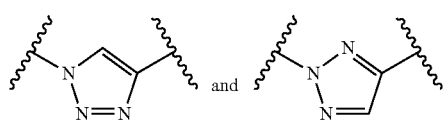 [SMILES: *c1cn(*)nn1 ; *c1cnn(*)n1]

In one embodiment $R^1$ is a group $C(O)OR^4$ in which $R^4$ is isopropyl.

In one embodiment $R^1$ is selected from

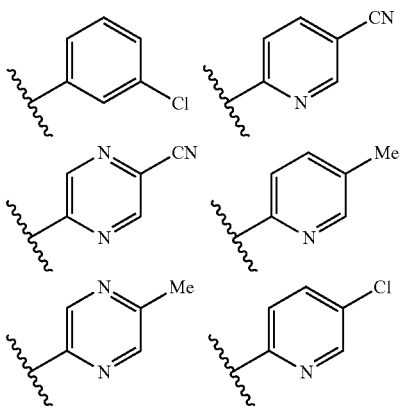

In one embodiment $R^2$ is methyl.
In one embodiment $R^3$ is methyl.
In one embodiment m is 1.
In one embodiment $R^5$ is hydrogen.
In one embodiment $R^6$ is methyl.

As used herein, the term "substituted" refers to substitution with the named substituent or substituents, multiple degrees of substitution being allowed unless otherwise stated. When the substituent is on a ring comprising a heteroatom the substituent may be located on a carbon or a heteroatom, if the latter is appropriate.

While the embodiments for each variable have generally been listed above separately for each variable, this invention is intended to include all combinations of embodiments described hereinabove including salts thereof.

Particular compounds according to the invention are:
1-methylethyl ((2S,4R)-1-acetyl-2-methyl-6-{1-[2-(methyloxy)ethyl]-1H-pyrazol-4-yl}-1,2,3,4-tetrahydro-4-quinolinyl)carbamate;
6-(((2S,4R)-1-acetyl-6-(1-(2-methoxyethyl)-1H-pyrazol-4-yl)-2-methyl-1,2,3,4-tetrahydroquinolin-4-yl)amino) nicotinonitrile;
6-(((2S,4R)-1-acetyl-6-(1-(2-methoxyethyl)-1H-1,2,3-triazol-4-yl)-2-methyl-1,2,3,4-tetrahydroquinolin-4-yl) amino)nicotinonitrile;
6-(((2S,4R)-1-acetyl-6-(2-(2-methoxyethyl)-2H-1,2,3-triazol-4-yl)-2-methyl-1,2,3,4-tetrahydroquinolin-4-yl) amino)nicotinonitrile;
1-((2S,4R)-4-((5-chloropyridin-2-yl)amino)-6-(1-(2-methoxyethyl)-1H-pyrazol-4-yl)-2-methyl-3,4-dihydroquinolin-1(2H)-yl);
1-((2S,4R)-6-(1-(2-methoxyethyl)-1H-pyrazol-4-yl)-2-methyl-4-((5-methylpyridin-2-yl)amino)-3,4-dihydroquinolin-1(2H)- yl)ethanone;
1-((2S,4R)-4-((3-chlorophenyl)amino)-6-(1-(2-methoxyethyl)-1H-pyrazol-4-yl)-2-methyl-3,4-dihydroquinolin-1 (2H)-yl); and
1-((2S,4R)-6-(1-(2-methoxyethyl)-1H-pyrazol-4-yl)-2-methyl-4-((5-methylpyrazin-2-yl)amino)-3,4-dihydroquinolin-1(2H)- yl)ethanone
or a salt thereof.

Throughout the present specification, unless otherwise stated:
the term "halogen" is used to describe a group selected from fluorine, chlorine or bromine;
the terms "$C_{1-3}$alkyl" and "$C_{1-4}$alkyl" are used to describe a group or a part of the group comprising a linear or branched alkyl group containing from 1 to 3 or 1 to 4 carbon atoms respectively. Other references are to be similarly interpreted. Suitable examples of such groups include methyl, ethyl, propyl, isopropyl, n-butyl, isobutyl and t-butyl;

the term "$C_{3-7}$cycloalkyl" is used to describe a non-aromatic carbocyclic ring containing at least three and at most seven carbon atoms. Examples of $C_{3-7}$cycloalkyl include cyclopropyl, cyclobutyl, cyclopentyl, cyclohexyl and cycloheptyl.

It will be appreciated that the present invention covers compounds of formula (I) as the free base and as salts thereof, for example as a pharmaceutically acceptable salt thereof. In one embodiment the invention relates to compounds of formula (I) or a pharmaceutically acceptable salt thereof. In an alternative embodiment the invention relates to compounds of formula (I) in the form of a free base.

Because of their potential use in medicine, salts of the compounds of formula (I) are desirably pharmaceutically acceptable. Suitable pharmaceutically acceptable salts can include acid addition salts. As used herein, the term 'pharmaceutically acceptable salt' means any pharmaceutically acceptable salt or solvate of a compound of formula (I), which upon administration to the recipient is capable of providing (directly or indirectly). In one embodiment, the term 'pharmaceutically acceptable salt' means any pharmaceutically acceptable salt of a compound of formula (I), which upon administration to the recipient is capable of providing (directly or indirectly). For a review on suitable salts see Berge et al., J. Pharm. Sci., 66:1-19, (1977). Typically, a pharmaceutically acceptable salt may be readily prepared by using a desired acid or base as appropriate. The resultant salt may precipitate from solution and be collected by filtration or may be recovered by evaporation of the solvent.

A pharmaceutically acceptable acid addition salt can be formed by reaction of a compound of formula (I) with a suitable inorganic or organic acid (such as hydrobromic, hydrochloric, sulphuric, nitric, phosphoric, succinc, maleic, acetic, propionic, fumaric, citric, tartaric, lactic, benzoic, salicylic, glutamaic, aspartic, p-toluenesulfonic, benzenesulfonic, methanesulfonic, ethanesulfonic, naphthalenesulfonic such as 2-naphthalenesulfonic, or hexanoic acid), optionally in a suitable solvent such as an organic solvent, to give the salt which is usually isolated for example by crystallisation and filtration. A pharmaceutically acceptable acid addition salt of a compound of formula (I) can comprise or be for example a hydrobromide, hydrochloride, sulfate, nitrate, phosphate, succinate, maleate, acetate, propionate, fumarate, citrate, tartrate, lactate, benzoate, salicylate, glutamate, aspartate, p-toluenesulfonate, benzenesulfonate, methanesulfonate, ethanesulfonate, naphthalenesulfonate (e.g. 2-naphthalenesulfonate) or hexanoate salt.

Other non-pharmaceutically acceptable salts, e.g. formates, oxalates or trifluoroacetates, may be used, for example in the isolation of the compounds of formula (I), and are included within the scope of this invention.

The invention includes within its scope all possible stoichiometric and non-stoichiometric forms of the salts of the compounds of formula (I).

It will be appreciated that many organic compounds can form complexes with solvents in which they are reacted or from which they are precipitated or crystallized. These complexes are known as "solvates". For example, a complex with water is known as a "hydrate". Solvents with high boiling points and/or capable of forming hydrogen bonds such as water, xylene, N-methyl pyrrolidinone, methanol and ethanol may be used to form solvates. Methods for identification of solvates include, but are not limited to, NMR and microanalysis. Solvates of the compounds of formula (I) are within the scope of the invention.

The invention includes within its scope all possible stoichiometric and non-stoichiometric forms of the solvates of the compounds of formula (I).

The compounds of formula (I) may be in crystalline or amorphous form. Furthermore, some of the crystalline forms of the compounds of formula (I) may exist as polymorphs, which are included within the scope of the present invention. Polymorphic forms of compounds of formula (I) may be characterized and differentiated using a number of conventional analytical techniques, including, but not limited to, X-ray powder diffraction (XRPD) patterns, infrared (IR) spectra, Raman spectra, differential scanning calorimetry (DSC), thermogravimetric analysis (TGA) and solid state nuclear magnetic resonance (SSNMR).

Certain compounds described herein contain chiral atoms so that optical isomers, e.g. enantiomers or diastereoisomers may be formed. Accordingly, the present invention encompasses all isomers of the compounds of formula (I) whether as individual isomers isolated such as to be substantially free of the other isomer (i.e. pure) or as mixtures (i.e. racemates and racemic mixtures). An individual isomer isolated such as to be substantially free of the other isomer (i.e. pure) may be isolated such that less than 10%, particularly less than about 1%, for example less than about 0.1% of the other isomer is present.

Separation of isomers may be achieved by conventional techniques known to those skilled in the art, e.g. by fractional crystallisation, chromatography or HPLC.

Certain compounds of formula (I) may exist in one of several tautomeric forms. It will be understood that the present invention encompasses all tautomers of the compounds of formula (I) whether as individual tautomers or as mixtures thereof.

It will be appreciated from the foregoing that included within the scope of the invention are solvates, isomers and polymorphic forms of the compounds of formula (I) and salts thereof.

The compounds of formula (I) or salts thereof may be made by a variety of methods, including standard chemistry. Any previously defined variable will continue to have the previously defined meaning unless otherwise indicated. Illustrative general synthetic methods are set out below and then specific compounds of formula (I) and salts thereof, are prepared in the Examples.

In a further aspect there is provided a process for the preparation of a compound of formula (I) which comprises a process selected from (a), (b), (c) and (d) in which
(a) comprises reacting a compound of formula (II)

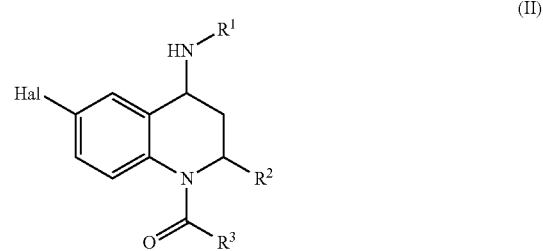

(II)

in which R$^1$, R$^2$ and R$^3$ are as defined in formula (I) and Hal is chlorine, bromine or iodine, with a compound of formula (III)

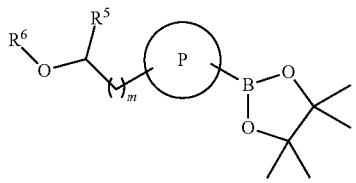
(III)

in which P, m, R$^5$ and R$^6$ are as defined in formula (I).

(b) comprises reacting a compound of formula (IV)

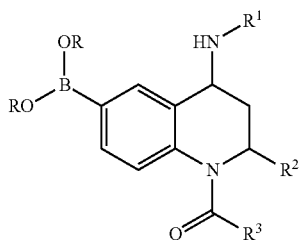
(IV)

in which R$^1$, R$^2$ and R$^3$ are as defined in formula (I) and R is H or B(OR)$_2$ is pinacolatoborane, with a compound of formula (V)

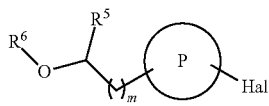
(V)

in which P, m, R$^5$ and R$^6$ are as defined in formula (I) and Hal is chlorine, bromine or iodine.

(c) comprises reacting a compound of formula (VI)

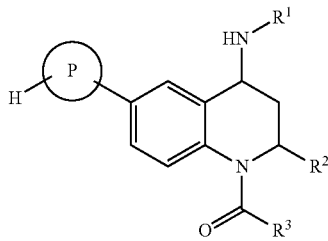
(VI)

in which P, R$^1$, R$^2$ and R$^3$ are as defined in formula (I), with a compound of formula (VII)

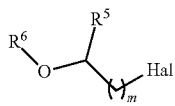
(VII)

in which m, R$^5$ and R$^6$ are as defined in formula (I) and Hal is halogen;

(d) comprises reacting a compound of formula (VIII)

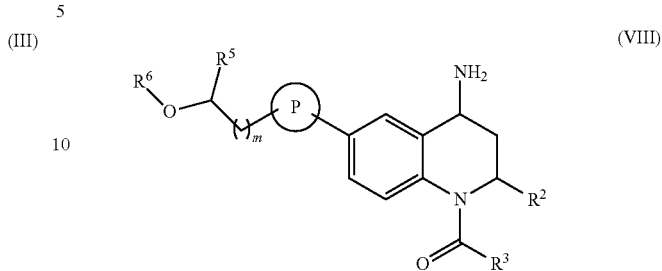
(VIII)

in which m, P, R$^2$, R$^3$, R$^5$, and R$^6$ are as defined in formula (I) with a compound of formula (IX)

(IX)

in which R$^1$ is as defined in formula (I) and Hal is halogen.

Process (a)

For process (a), a suitable halogen is bromine. This reaction may be carried out by stirring a compound of formula (II) with a compound of formula (III) in the presence of a suitable palladium catalyst such as Pd(PPh$_3$)$_4$, a base such as aqueous sodium or potassium carbonate in a suitable organic solvent such as ethanol or toluene or a combination thereof.

Compounds of formula (II) and (III) can be prepared by methods described herein or by analogous methods thereto.

Process (b)

For process (a), a suitable halogen is bromine. This reaction may be carried out by stirring a compound of formula (IV) with a compound of formula (V) in the presence of a suitable palladium catalyst such as Pd(PPh$_3$)$_4$, a base such as aqueous sodium or potassium carbonate in a suitable organic solvent such as ethanol or toluene or a combination thereof.

Process (c)

For process (c), a suitable halogen is bromine. The reaction between the compound of formula (VI) and formula (VII) may be carried out in a suitable organic solvent such as DMF, in the presence of a base such as potassium carbonate.

Compounds of formula (VI) and (VII) can be prepared by methods described herein or by analogous methods thereto.

Process (d)

For process (d), a suitable halogen is bromine. The reaction between the compound of formula (VIII) and formula (IX) may be carried out in a suitable organic solvent such as dioxane, in the presence of a palladium catalyst such as tris (dibenzyldieneacetone)dipalladium(0), a phosphine ligand a base such as sodium tert-butoxide.

Compounds of formula (VIII) can be prepared by methods described herein or by analogous methods thereto. Compounds of formula (IX) are commercially available.

It will be appreciated by those skilled in the art that it may be advantageous to protect one or more functional groups of the compounds described above. Examples of protecting groups and the means for their removal can be found in T. W. Greene 'Protective Groups in Organic Synthesis' (4th edition, J. Wiley and Sons, 2006). Suitable amine protecting groups include acyl (e.g. acetyl, carbamate (e.g. 2',2',2'-trichloroethoxycarbonyl, benzyloxycarbonyl or t-butoxycarbonyl) and arylalkyl (e.g. benzyl), which may be removed by hydrolysis (e.g. using an acid such as hydrochloric acid in dioxane or trifluoroacetic acid in dichloromethane) or reductively (e.g. hydrogenolysis of a benzyl or benzyloxycarbonyl group or reductive removal of a 2',2',2'-trichloroethoxycarbonyl group using zinc in acetic acid) as appropriate. Other suitable amine protecting groups include trifluoroacetyl (—COCF$_3$) which may be removed by base catalysed hydrolysis.

It will be appreciated that in any of the routes described above, the precise order of the synthetic steps by which the various groups and moieties are introduced into the molecule may be varied. It will be within the skill of the practitioner in the art to ensure that groups or moieties introduced at one stage of the process will not be affected by subsequent transformations and reactions, and to select the order of synthetic steps accordingly.

Certain intermediate compounds described above form a yet further aspect of the invention.

The compounds of formula (I) and salts thereof are bromodomain inhibitors, and thus are believed to have potential utility in the treatment of diseases or conditions for which a bromodomain inhibitor is indicated.

The present invention thus provides a compound of formula (I) or a pharmaceutically acceptable salt thereof for use in therapy. The compound of formula (I) or a pharmaceutically salt thereof can be used in the treatment of diseases or conditions for which a bromodomain inhibitor is indicated.

The present invention thus provides a compound of formula (I) or a pharmaceutically acceptable salt thereof for use in the treatment of any diseases or conditions for which a bromodomain inhibitor is indicated. In another embodiment there is provided a compound or a pharmaceutically acceptable salt thereof for use in the treatment of chronic autoimmune and/or inflammatory conditions. In a further embodiment there is provided a compound or a pharmaceutically acceptable salt thereof for use in the treatment of cancer.

Also provided is the use of a compound of formula (I) or a pharmaceutically acceptable salt thereof in the manufacture of a medicament for the treatment of diseases or conditions for which a bromodomain inhibitor is indicated.

Also provided is a method of treating diseases or conditions for which a bromodomain inhibitor is indicated in a subject in need thereof which comprises administering a therapeutically effective amount of compound of formula (I) or a pharmaceutically acceptable salt thereof.

Suitably the subject in need thereof is a human.

As used herein, the term "effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

Bromodomain inhibitors are believed to be useful in the treatment of a variety of diseases or conditions related to systemic or tissue inflammation, inflammatory responses to infection or hypoxia, cellular activation and proliferation, lipid metabolism, fibrosis and in the prevention and treatment of viral infections.

Bromodomain inhibitors may be useful in the treatment of a wide variety of chronic autoimmune and inflammatory conditions such as rheumatoid arthritis, osteoarthritis, acute gout, psoriasis, systemic lupus erythematosus, multiple sclerosis, inflammatory bowel disease (Crohn's disease and Ulcerative colitis), asthma, chronic obstructive airways disease, pneumonitis, myocarditis, pericarditis, myositis, eczema, dermatitis (including atopic dermatitis), alopecia, vitiligo, bullous skin diseases, nephritis, vasculitis, atherosclerosis, Alzheimer's disease, depression, Sjögren's syndrome, sialoadenitis, central retinal vein occlusion, branched retinal vein occlusion, Irvine-Gass syndrome (post cataract and post-surgical), retinitis pigmentosa, pars planitis, birdshot retinochoroidopathy, epiretinal membrane, cystic macular edema, parafoveal telengiectasis, tractional maculopathies, vitreomacular traction syndromes, retinal detachment, neuroretinitis, idiopathic macular edema, retinitis, dry eye (kerartoconjunctivitis Sicca), vernal keratoconjunctivitis, atopic keratoconjunctivitis, anterior uveitis, pan uveitis, posterior uveits, uveitis-associated macula edema. scleritis, diabetic retinopathy, diabetic macula edema, age-related macula dystrophy, hepatitis, pancreatitis, primary biliary cirrhosis, sclerosing cholangitis, Addison's disease, hypophysitis, thyroiditis, type I diabetes and acute rejection of transplanted organs.

Bromodomain inhibitors may be useful in the treatment of a wide variety of acute inflammatory conditions such as acute gout, giant cell arteritis, nephritis including lupus nephritis, vasculitis with organ involvement such as glomerulonephritis, vasculitis including giant cell arteritis, Wegener's granulomatosis, Polyarteritis nodosa, Behcet's disease, Kawasaki disease, Takayasu's Arteritis, pyoderma gangrenosum, vasculitis with organ involvement and acute rejection of transplanted organs.

Bromodomain inhibitors may be useful in the prevention or treatment of diseases or conditions which involve inflammatory responses to infections with bacteria, viruses, fungi, parasites or their toxins, such as sepsis, sepsis syndrome, septic shock, endotoxaemia, systemic inflammatory response syndrome (SIRS), multi-organ dysfunction syndrome, toxic shock syndrome, acute lung injury, ARDS (adult respiratory distress syndrome), acute renal failure, fulminant hepatitis, burns, acute pancreatitis, post-surgical syndromes, sarcoidosis, Herxheimer reactions, encephalitis, myelitis, meningitis, malaria and SIRS associated with viral infections such as influenza, herpes zoster, herpes simplex and coronavirus.

Bromodomain inhibitors may be useful in the prevention or treatment of conditions associated with ischaemia-reperfusion injury such as myocardial infarction, cerebro-vascular ischaemia (stroke), acute coronary syndromes, renal reperfusion injury, organ transplantation, coronary artery bypass grafting, cardio-pulmonary bypass procedures, pulmonary, renal, hepatic, gastro-intestinal or peripheral limb embolism.

Bromodomain inhibitors may be useful in the treatment of disorders of lipid metabolism via the regulation of APO-A1 such as hypercholesterolemia, atherosclerosis and Alzheimer's disease.

Bromodomain inhibitors may be useful in the treatment of fibrotic conditions such as
idiopathic pulmonary fibrosis, renal fibrosis, post-operative stricture, keloid scar formation, scleroderma (including morphea) and cardiac fibrosis.

Bromodomain inhibitors may be useful in the prevention and treatment of viral infections such as herpes virus, human papilloma virus, adenovirus and poxvirus and other DNA viruses.

Bromodomain inhibitors may be useful in the treatment of cancer, including hematological (such as leukaemia, lymphoma and multiple myeloma), epithelial (including lung, breast and colon carcinomas), midline carcinomas, mesenchymal, hepatic, renal and neurological tumours. In one embodiment the cancer is NUT-midline carcinoma.

Bromodomain inhibitors may be useful in the treatment of dermal pathology such as non-malignant melanoma (actinic keratosis and basal cell), in-situ melanoma, squamous cell carcinoma and cutaneous T-cell lymphoma.

In one embodiment the disease or condition for which a bromodomain inhibitor is indicated is selected from diseases associated with systemic inflammatory response syndrome, such as sepsis, burns, pancreatitis, major trauma, haemorrhage and ischaemia. In this embodiment the bromodomain inhibitor would be administered at the point of diagnosis to reduce the incidence of: SIRS, the onset of shock, multi-organ dysfunction syndrome, which includes the onset of acute lung injury, ARDS, acute renal, hepatic, cardiac and gastro-intestinal injury and mortality. In another embodiment the bromodomain inhibitor would be administered prior to surgical or other procedures associated with a high risk of sepsis, haemorrhage, extensive tissue damage, SIRS or MODS (multiple organ dysfunction syndrome). In a particular embodiment the disease or condition for which a bromodomain inhibitor is indicated is sepsis, sepsis syndrome, septic shock and endotoxaemia. In another embodiment, the bromodomain inhibitor is indicated for the treatment of acute or chronic pancreatitis. In another embodiment the bromodomain is indicated for the treatment of burns.

In one embodiment the disease or condition for which a bromodomain inhibitor is indicated is selected from herpes simplex infections and reactivations, cold sores, herpes zoster infections and reactivations, chickenpox, shingles, human papilloma virus, human immunodeficiency virus (HIV), cervical neoplasia, adenovirus infections, including acute respiratory disease, poxvirus infections such as cowpox and smallpox and African swine fever virus. In one particular embodiment a bromodomain inhibitor is indicated for the treatment of Human papilloma virus infections of skin or cervical epithelia. In a further embodiment the bromodomain inhibitor is indicated for the treatment of latent HIV infection.

The term "diseases or conditions for which a bromodomain inhibitor is indicated", is intended to include each of or all of the above disease states.

The invention further provides for a method for inhibiting a bromodomain which comprises contacting the bromodomain with a compound of formula (I) or a pharmaceutically acceptable salt thereof.

While it is possible that for use in therapy, a compound of formula (I) as well as pharmaceutically acceptable salts thereof may be administered as the raw chemical, it is common to present the active ingredient as a pharmaceutical composition.

The present invention therefore provides in a further aspect a pharmaceutical composition comprising a compound of formula (I) or a pharmaceutically acceptable salt and one or more pharmaceutically acceptable carriers, diluents or excipients. The compounds of formula (I) and pharmaceutically acceptable salts, are as described above. The carrier(s), diluent(s) or excipient(s) must be acceptable in the sense of being compatible with the other ingredients of the composition and not deleterious to the recipient thereof. In accordance with another aspect of the invention there is also provided a process for the preparation of a pharmaceutical composition including admixing a compound of formula (I), or a pharmaceutically acceptable salt thereof, with one or more pharmaceutically acceptable carriers, diluents or excipients. The pharmaceutical composition can be used in the treatment of any of the conditions described herein.

Since the compounds of formula (I) are intended for use in pharmaceutical compositions it will be readily understood that they are each preferably provided in substantially pure form, for example, at least 60% pure, more suitably at least 75% pure and preferably at least 85% pure, especially at least 98% pure (% in a weight for weight basis).

Pharmaceutical compositions may be presented in unit dose forms containing a predetermined amount of active ingredient per unit dose. Preferred unit dosage compositions are those containing a daily dose or sub-dose, or an appropriate fraction thereof, of an active ingredient. Such unit doses may therefore be administered more than once a day. Preferred unit dosage compositions are those containing a daily dose or sub-dose (for administration more than once a day), as herein above recited, or an appropriate fraction thereof, of an active ingredient.

Pharmaceutical compositions may be adapted for administration by any appropriate route, for example by the oral (including buccal or sublingual), rectal, inhaled, intranasal, topical (including buccal, sublingual or transdermal), ocular (including topical, intraocular, subconjunctival, episcleral, sub-Tenon), vaginal or parenteral (including subcutaneous, intramuscular, intravenous or intradermal) route. Such compositions may be prepared by any method known in the art of pharmacy, for example by bringing into association the active ingredient with the carrier(s) or excipient(s).

In one embodiment the pharmaceutical composition is adapted for parenteral administration, particularly intravenous administration.

In one embodiment the pharmaceutical composition is adapted for oral administration.

In one embodiment the pharmaceutical composition is adapted for topical administration.

A preferred dosage form that results in occlusion and modification of skin permeation either to increase or decrease the systemic exposure of bromodomain compounds, including but not limited to the pharmaceutically acceptable forms of carboxymethylcellulose, an aliginate, gelatin or polyvinyl pyrrolidone.

Pharmaceutical compositions adapted for parenteral administration include aqueous and non-aqueous sterile injection solutions which may contain anti-oxidants, buffers, bacteriostats and solutes which render the composition isotonic with the blood of the intended recipient; and aqueous and non-aqueous sterile suspensions which may include suspending agents and thickening agents. The compositions may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

Pharmaceutical compositions adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

For instance, for oral administration in the form of a tablet or capsule, the active drug can be combined with an oral, non-toxic pharmaceutically acceptable inert carrier such as ethanol, glycerol, water and the like. Powders suitable for incorporating into tablets or capsules may be prepared by reducing the compound to a suitable fine size (e.g. by micronisation) and mixing with a similarly prepared pharmaceutical carrier such as an edible carbohydrate, for example, starch or mannitol. Flavoring, preservative, dispersing and coloring agent can also be present.

Capsules may be made by preparing a powder mixture, as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, glidants, lubricants, sweetening agents, flavours, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of formula (I) and pharmaceutically acceptable salts thereof, can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Where appropriate, dosage unit compositions for oral administration can be microencapsulated. The formulation can also be prepared to prolong or sustain the release as for example by coating or embedding particulate material in polymers, wax or the like.

The compounds of formula (I) and pharmaceutically acceptable salts thereof, can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Pharmaceutical compositions adapted for topical administration may be formulated as ointments, creams, suspensions, emulsions, lotions, powders, solutions, pastes, gels, foams, sprays, aerosols or oils. Such pharmaceutical compositions may include conventional additives which include, but are not limited to, preservatives, solvents to assist drug penetration, co-solvents, emollients, propellants, viscosity modifying agents (gelling agents), surfactants and carriers. In one embodiment there is provided a pharmaceutical composition adapted for topical administration which comprises between 0.01-10%, or between 0.01-1% of the compound of formula (I), or a pharmaceutically acceptable salt thereof, by weight of the composition.

For treatments of the eye or other external tissues, for example mouth and skin, the compositions are preferably applied as a topical solution, suspension, emulsion, ointment, cream, gel, spray or foam. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical compositions adapted for topical administrations to the eye include eye drops wherein the active ingredient is dissolved or suspended in a suitable carrier, especially an aqueous solvent. Compositions to be administered to the eye will have ophthalmically compatible pH and osmolality. One or more ophthalmically acceptable pH adjusting agents and/or buffering agents can be included in a composition of the invention, including acids such as acetic, boric, citric, lactic, phosphoric and hydrochloric acids; bases such as sodium hydroxide, sodium phosphate, sodium borate, sodium citrate, sodium acetate, and sodium lactate; and buffers such as citrate/dextrose, sodium bicarbonate and ammonium chloride. Such acids, bases, and buffers can be included in an amount required to maintain pH of the composition in an ophthalmically acceptable range. One or more ophthalmically acceptable salts can be included in the composition in an amount sufficient to bring osmolality of the composition into an ophthalmically acceptable range. Such salts include those having sodium, potassium or ammonium cations and chloride, citrate, ascorbate, borate, phosphate, bicarbonate, sulfate, thiosulfate or bisulfite anions.

The ocular delivery device may be designed for the controlled release of one or more therapeutic agents with multiple defined release rates and sustained dose kinetics and permeability. Controlled release may be obtained through the design of polymeric matrices incorporating different choices and properties of biodegradable/bioerodable polymers (e.g. poly(ethylene vinyl) acetate (EVA), superhydrolyzed PVA), hydroxyalkyl cellulose (HPC), methylcellulose (MC), hydroxypropyl methyl cellulose (HPMC), polycaprolactone, poly(glycolic) acid, poly(lactic) acid, polyanhydride, of polymer molecular weights, polymer crystallinity, copolymer ratios, processing conditions, surface finish, geometry, excipient addition and polymeric coatings that will enhance drug diffusion, erosion, dissolution and osmosis.

Pharmaceutical compositions for ocular delivery also include in situ gellable aqueous composition. Such a composition comprises a gelling agent in a concentration effective to promote gelling upon contact with the eye or with lacrimal fluid. Suitable gelling agents include but are not limited to thermosetting polymers. The term "in situ gellable" as used herein is includes not only liquids of low viscosity that form gels upon contact with the eye or with lacrimal fluid, but also includes more viscous liquids such as semi-fluid and thixotropic gels that exhibit substantially increased viscosity or gel stiffness upon administration to the eye. See, for example, Ludwig (2005) Adv. Drug Deliv. Rev. 3; 57:1595-639, herein incorporated by reference for purposes of its teachings of examples of polymers for use in ocular drug delivery.

Dosage forms for nasal or inhaled administration may conveniently be formulated as aerosols, solutions, suspensions, gels or dry powders.

For compositions suitable and/or adapted for inhaled administration, it is preferred that the compound of formula (I) or a pharmaceutically acceptable salt thereof, is in a particle-size-reduced form e.g. obtained by micronisation. The preferable particle size of the size-reduced (e.g. micronised) compound or salt is defined by a D50 value of about 0.5 to about 10 microns (for example as measured using laser diffraction).

Aerosol formulations, e.g. for inhaled administration, can comprise a solution or fine suspension of the active substance in a pharmaceutically acceptable aqueous or non-aqueous solvent. Aerosol formulations can be presented in single or multidose quantities in sterile form in a sealed container, which can take the form of a cartridge or refill for use with an atomising device or inhaler. Alternatively the sealed container may be a unitary dispensing device such as a single dose nasal inhaler or an aerosol dispenser fitted with a metering valve (metered dose inhaler) which is intended for disposal once the contents of the container have been exhausted.

Where the dosage form comprises an aerosol dispenser, it preferably contains a suitable propellant under pressure such as compressed air, carbon dioxide or an organic propellant such as a hydrofluorocarbon (HFC). Suitable HFC propellants include 1,1,1,2,3,3,3-heptafluoropropane and 1,1,1,2-tetrafluoroethane. The aerosol dosage forms can also take the form of a pump-atomiser. The pressurised aerosol may contain a solution or a suspension of the active compound. This may require the incorporation of additional excipients e.g. co-solvents and/or surfactants to improve the dispersion characteristics and homogeneity of suspension formulations. Solution formulations may also require the addition of co-solvents such as ethanol.

For pharmaceutical compositions suitable and/or adapted for inhaled administration, the pharmaceutical composition may be a dry powder inhalable composition. Such a composition can comprise a powder base such as lactose, glucose, trehalose, mannitol or starch, the compound of formula (I) or a pharmaceutically acceptable salt thereof (preferably in particle-size-reduced form, e.g. in micronised form), and optionally a performance modifier such as L-leucine or another amino acid and/or metals salts of stearic acid such as magnesium or calcium stearate. Preferably, the dry powder inhalable composition comprises a dry powder blend of lactose e.g. lactose monohydrate and the compound of formula (I) or salt thereof. Such compositions can be administered to the patient using a suitable device such as the DISKUS® device, marketed by GlaxoSmithKline which is for example described in GB 2242134 A.

The compounds of formula (I) and pharmaceutically acceptable salts thereof may be formulated as a fluid formulation for delivery from a fluid dispenser, for example a fluid dispenser having a dispensing nozzle or dispensing orifice through which a metered dose of the fluid formulation is dispensed upon the application of a user-applied force to a pump mechanism of the fluid dispenser. Such fluid dispensers are generally provided with a reservoir of multiple metered doses of the fluid formulation, the doses being dispensable upon sequential pump actuations. The dispensing nozzle or orifice may be configured for insertion into the nostrils of the user for spray dispensing of the fluid formulation into the nasal cavity. A fluid dispenser of the aforementioned type is described and illustrated in WO-A-2005/044354.

A therapeutically effective amount of a compound of formula (I) or a pharmaceutically acceptable salt thereof, will depend upon a number of factors including, for example, the age and weight of the animal, the precise condition requiring treatment and its severity, the nature of the formulation, and the route of administration, and will ultimately be at the discretion of the attendant physician or veterinarian. In the pharmaceutical composition, each dosage unit for oral or parenteral administration preferably contains from 0.01 to 3000 mg, more preferably 0.5 to 1000 mg, of a compound of formula (I) or a pharmaceutically acceptable salt thereof, calculated as the free base. Each dosage unit for nasal or inhaled administration preferably contains from 0.001 to 50 mg, more preferably 0.01 to 5 mg, of a compound of the formula (I) or a pharmaceutically acceptable salt thereof, calculated as the free base.

The pharmaceutically acceptable compounds of formula (I) and pharmaceutically acceptable salts thereof, can be administered in a daily dose (for an adult patient) of, for example, an oral or parenteral dose of 0.01 mg to 3000 mg per day or 0.5 to 1000 mg per day, or a nasal or inhaled dose of 0.001 to 50 mg per day or 0.01 to 5 mg per day, of the compound of the formula (I) or a pharmaceutically acceptable salt thereof, calculated as the free base. This amount may be given in a single dose per day or more usually in a number (such as two, three, four, five or six) of sub-doses per day such that the total daily dose is the same. An effective amount of a salt thereof, may be determined as a proportion of the effective amount of the compound of formula (I) per se.

The compounds of formula (I) and pharmaceutically acceptable salts thereof, and may be employed alone or in combination with other therapeutic agents. Combination therapies according to the present invention thus comprise the administration of at least one compound of formula (I) or a pharmaceutically acceptable salt thereof, and the use of at least one other theraputically active agent. Preferably, combination therapies according to the present invention comprise the administration of at least one compound of formula (I) or a pharmaceutically acceptable salt thereof, and at least one other therapeutically active agent. The compound(s) of formula (I) and pharmaceutically acceptable salts thereof, and the other therapeutically active agent(s) may be administered together in a single pharmaceutical composition or separately and, when administered separately this may occur simultaneously or sequentially in any order. The amounts of the compound(s) of formula (I) and pharmaceutically acceptable salts thereof, and the other therapeutically active agent(s) and the relative timings of administration will be selected in order to achieve the desired combined therapeutic effect. Thus in a further aspect, there is provided a combination comprising a compound of formula (I) or a pharmaceutically acceptable salt thereof, and at least one other therapeutically active agent.

Thus in one aspect, the compound of formula (I) or a pharmaceutically acceptable salt thereof, and pharmaceutical compositions comprising a compound of formula (I) or a pharmaceutically acceptable salt thereof, according to the invention may be used in combination with or include one or more other therapeutic agents, for example selected from antibiotics, anti-virals, glucocorticosteroids, muscarinic antagonists beta-2 agonists and Vitamin D3 analogues. In a further aspect a compound of formula (I) or a pharmaceutically acceptable salt thereof, according to the invention may be used in combination with a further therapeutic agent which is suitable for the treatment of cancer It will be appreciated that when the compound of formula (I) or a pharmaceutically acceptable salt thereof, is administered in combination with other therapeutic agents normally administered by the inhaled, intravenous, oral or intranasal route, that the resultant pharmaceutical composition may be administered by the same routes. Alternatively the individual components of the composition may be administered by different routes.

One embodiment of the invention encompasses combinations comprising one or two other therapeutic agents.

It will be clear to a person skilled in the art that, where appropriate, the other therapeutic ingredient(s) may be used in the form of salts, for example as alkali metal or amine salts or as acid addition salts, or prodrugs, or as esters, for example lower alkyl esters, or as solvates, for example hydrates, to optimise the activity and/or stability and/or physical characteristics, such as solubility, of the therapeutic ingredient. It will be clear also that, where appropriate, the therapeutic ingredients may be used in optically pure form.

The combinations referred to above may conveniently be presented for use in the form of a pharmaceutical composition and thus pharmaceutical compositions comprising a combination as defined above together with a pharmaceutically acceptable diluent or carrier represent a further aspect of the invention.

The compounds of formula (I) and pharmaceutically acceptable salts thereof, may be prepared by the methods described below or by similar methods. Thus the following Intermediates and Examples serve to illustrate the preparation of the compounds of formula (I) and pharmaceutically acceptable salts thereof, and are not to be considered as limiting the scope of the invention in any way.

GENERAL EXPERIMENTAL DETAILS

All temperatures referred to are in ° C. The names of the following compounds have been obtained using the compound naming programme "ACD Name Pro 6.02" or Chem Draw Ultra 12.0.

Abbreviations
BINAP 2,2'-bis(diphenylphosphino)-1,1'-binaphthyl
CV column volumes
Dave phos [2'-(dicyclohexylphosphanyl)-2-biphenylyl]dimethylamine
DCM dichloromethane
DIPEA Diisopropylethylamine
DMF N,N-dimethylformamide
DMSO dimethylsulfoxide
EtOAc ethyl acetate
EtOH ethanol
h hour(s)
KOH potassium hydroxide
LCMS liquid chromatography/mass spectrometry
MDAP Mass directed autoprep=preparative mass directed HPLC
min minute(s)
MgSO$_4$ magnesium sulphate
Na$_2$SO$_4$ sodium sulphate
NMP N-methyl-2-pyrrolidone
Pd$_2$(dba)$_3$ Tris(dibenzyldieneacetone)dipalladium(0)
r.t. room temperature
Rt retention time
TFA trifluoroacetic acid
THF tetrahydrofuran LCMS Methodology
Method Formate
LC Conditions The UPLC analysis was conducted on an Acquity UPLC BEH C18 column (50 mm×2.1 mm, i.d. 1.7 µm packing diameter) at 40° C.

The solvents employed were:
A=0.1% v/v solution of formic acid in water
B=0.1% v/v solution of formic acid in acetonitrile
The gradient employed was:

| Time (min) | Flow rate (ml/min) | % A | % B |
|---|---|---|---|
| 0 | 1 | 99 | 1 |
| 1.5 | 1 | 3 | 97 |
| 1.9 | 1 | 3 | 97 |
| 2.0 | 1 | 0 | 100 |

The UV detection was a summed signal from wavelength of 210 nm to 350 nm.
MS Conditions
MS: Waters ZQ
Ionisation mode: Alternate-scan positive and negative electrospray
Scan range: 100 to 1000 AMU
Scan time: 0.27 sec
Inter scan delay: 0.10 sec
Method HpH
LC Conditions The UPLC analysis was conducted on an Acquity UPLC BEH C18 column (50 mm×2.1 mm, i.d. 1.7 µm packing diameter) at 40° C.

The solvents employed were:
A=10 mM ammonium hydrogen carbonate in water adjusted to pH10 with ammonia solution
B=acetonitrile
The gradient employed was:

| Time (min) | Flow rate (ml/min) | % A | % B |
|---|---|---|---|
| 0 | 1 | 99 | 1 |
| 1.5 | 1 | 3 | 97 |
| 1.9 | 1 | 3 | 97 |
| 2.0 | 1 | 0 | 100 |

The UV detection was a summed signal from wavelength of 210 nm to 350 nm.
MS conditions
MS: Waters ZQ
Ionisation mode: Alternate-scan positive and negative electrospray
Scan range: 100 to 1000 AMU
Scan time: 0.27 sec
Inter scan delay: 0.10 sec
LCMS (Method B) was conducted on an Acquity UPLC BEH C18 column (50 mm×2.1 mm i.d. 1.7 µm packing diameter) at 40 degrees centigrade, eluting with 0.1% v/v solution of Formic Acid in Water (Solvent A) and 0.1% v/v solution of Formic Acid in Acetonitrile (Solvent B) using the following elution gradient 0-1.5 min 3-100% B, 1.5-1.9 min 100% B, 1.9-2.0 min 3% B at a flow rate of 1 ml/min. The UV detection was a summed signal from wavelength of 210 nm to 350 nm. The mass spectra were recorded on a Waters ZQ Mass Spectrometer using Alternate-scan Positive and Negative Electrospray. Ionisation data was rounded to the nearest integer.

LCMS (Method C) was conducted on an Acquity UPLC BEH C18 column (50 mm×2.1 mm i.d. 1.7 μm packing diameter) at 40 degrees centigrade, eluting with 0.1% v/v solution of Trifluoroacetic Acid in Water (Solvent A) and 0.1% v/v solution of Trifluoroacetic Acid in Acetonitrile (Solvent B) using the following elution gradient 0-1.5 min 3-100% B, 1.5-1.9 min 100% B, 1.9-2.0 min 3% B at a flow rate of 1 ml/min. The UV detection was a summed signal from wavelength of 210 nm to 350 nm. The mass spectra were recorded on a Waters ZQ Mass Spectrometer using Positive Electrospray. Ionisation data was rounded to the nearest integer.

MDAP Methodology

Method Formate

LC Conditions

The HPLC analysis was conducted on either a Sunfire C18 column (100 mm×19 mm, i.d 5 μm packing diameter) or a Sunfire C18 column (150 mm×30 mm, i.d. 5 μm packing diameter) at ambient temperature.

The solvents employed were:

A=0.1% v/v solution of formic acid in water

B=0.1% v/v solution of formic acid in acetonitrile

Run as a gradient over either 15 or 25 min (extended run) with a flow rate of 20 ml/min (100 mm×19 mm, i.d 5 μm packing diameter) or 40 ml/min (150 mm×30 mm, i.d. 5 μm packing diameter).

The UV detection was a summed signal from wavelength of 210 nm to 350 nm.

MS Conditions

MS: Waters ZQ

Ionisation mode: Alternate-scan positive and negative electrospray

Scan range: 100 to 1000 AMU

Scan time: 0.50 sec

Inter scan delay: 0.20 sec

Method HpH

LC Conditions

The HPLC analysis was conducted on either an Xbridge C18 column (100 mm×19 mm, i.d 5 μm packing diameter) or an Xbridge C18 column (100 mm×30 mm, i.d. 5 μm packing diameter) at ambient temperature.

The solvents employed were:

A=10 mM ammonium bicarbonate in water, adjusted to pH10 with ammonia solution

B=acetonitrile

Run as a gradient over either 15 or 25 min (extended run) with a flow rate of 20 ml/min (100 mm×19 mm, i.d 5 μm packing diameter) or 40 ml/min (100 mm×30 mm, i.d 5 μm packing diameter).

The UV detection was a summed signal from wavelength of 210 nm to 350 nm.

MS Conditions

MS: Waters ZQ

Ionisation mode: Alternate-scan positive and negative electrospray

Scan range: 100 to 1000 AMU

Scan time: 0.50 sec

Inter scan delay: 0.20 sec

Method TFA

LC Conditions

The HPLC analysis was conducted on either a Sunfire C18 column (100 mm×19 mm, i.d. 5 μm packing diameter) or Sunfire C18 column (150 mm×30 mm, i.d. 5 μm packing diameter) at ambient temperature.

The solvents employed were:

A=0.1% v/v solution of trifluoroacetic acid in water

B=0.1% v/v solution of trifluoroacetic in acetonitrile

Run as a gradient over either 15 or 25 min (extended run) with a flow rate of 20 ml/min (100 mm×19 mm, i.d 5 μm packing diameter) or 40 ml/min (150 mm×30 mm, i.d 5 μm packing diameter).

The UV detection was a summed signal from wavelength of 210 nm to 350 nm.

MS Conditions

MS: Waters ZQ

Ionisation mode: Positive electrospray

Scan range: 100 to 1000 AMU

Scan time: 0.50 sec

Inter scan delay: 0.20 sec

Preparative HPLC Methodology

Method HpH

LC Conditions

The HPLC analysis was conducted on an Xbridge C18 column (100 mm×30 mm, i.d. 5 μm packing diameter) at ambient temperature.

The solvents employed were:

A=10 mM ammonium bicarbonate in water, adjusted to pH10 with ammonia solution

B=acetonitrile

Run as a gradient over 30 min with a flow rate of 30 mL/min

The UV detection was a summed signal from wavelength of 210 nm to 350 nm.

Intermediate 1

1-Methylethyl [(2S,4R)-1-acetyl-6-bromo-2-methyl-1,2,3,4-tetrahydro-4-quinolinyl]carbamate

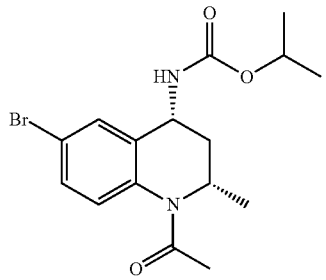 [SMILES: CC(=O)N1c2ccc(Br)cc2[C@H](NC(=O)OC(C)C)C[C@@H]1C]

1-Methylethyl [(2S,4R)-6-bromo-2-methyl-1,2,3,4-tetrahydro-4-quinolinyl]carbamate (for a preparation see Intermediate 2) (14.1 g, 43.1 mmol) was taken up in DCM (400 ml) under nitrogen at room temperature. Pyridine (10.46 ml, 129 mmol), then acetyl chloride (4.60 ml, 64.6 mmol), were added and the reaction stirred at room temperature for 16 h, then partitioned between ethyl acetate (2.0 l) and a saturated aqueous sodium hydrogen carbonate (800 ml). The layers were separated and the organic phase was washed with water then brine (1500 ml each) and then dried with $Na_2SO_4$ and concentrated in vacuo to yield a purple solid. The crude product was taken up in the minimum of DCM and applied to a 330 g Companion XL column and eluted with a gradient of 12-63% ethyl acetate in cyclohexane to give the product as an off-white solid (12.37 g).

LCMS (Method B), Rt 1.03 min, MH+ 369

[alpha]D=+281.1025° (T=20.7° C., 10 mm cell, c=0.508 g/100 ml, ethanol).

Intermediate 2

1-Methylethyl [(2S,4R)-6-bromo-2-methyl-1,2,3,4-tetrahydro-4-quinolinyl]carbamate

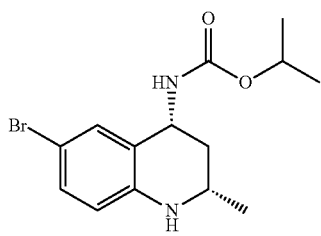 [SMILES: CC(C)OC(=O)N[C@@H]1C[C@H](C)Nc2ccc(Br)cc21]

1-Methylethyl {(3S)-3-[(4-bromophenyl)amino]butanoyl}carbamate (for a preparation see Intermediate 3) (17.9 g, 52.2 mmol) was taken up in ethanol (150 ml) and cooled to below −10° C. (internal temperature) in a $CO_2$/acetone bath. Sodium borohydride (1.381 g, 36.5 mmol) was added followed by magnesium chloride hexahydrate (11.35 g, 55.8 mmol) in water (25 ml) keeping the temperature below −5° C. The mixture was allowed to stir at <0° C. for 1 h then warmed to room temperature and stirred for 1 h. The resulting thick suspension was poured into a mixture of citric acid (25.05 g, 130 mmol), hydrochloric acid (1M, 205 ml, 205 mmol) and DCM (205 ml). The biphasic mixture was stirred at room temperature for 1 h. The layers were separated and the organic layer dried with $Na_2SO_4$, filtered and concentrated to yield the product as a light brown solid (14.1 g). LCMS (Method B), Rt 1.13 min, MH+ 327

Intermediate 3

1-Methylethyl {(3S)-3-[(4-bromophenyl)amino]butanoyl}carbamate

1-Methylethyl (2E)-2-butenoylcarbamate (for a preparation see Intermediate 4) (9.38 g, 54.8 mmol) was stirred in toluene (281 ml) under nitrogen and (R-BINAP)ditriflatebis(acetonitrile)palladium(II) (for a preparation see Intermediate 5) (3.35 g, 3.01 mmol) added. The catalyst formed a gummy ball, the solution turned to an opaque yellow mixture and was stirred for 20 min. 4-Bromoaniline (14.14 g, 82 mmol) was added, the solution turned to a clear light brown and the gummy catalyst dissolved further. The mixture was stirred for 16 h. Similarly a second batch of 1-methylethyl (2E)-2-butenoylcarbamate (Intermediate 4, 8.51 g, 49.7 mmol) was stirred in toluene (255 ml) under nitrogen and (R-BINAP)ditriflatebis(acetonitrile)palladium(II) (3.04 g, 2.73 mmol) added. The catalyst formed a gummy ball, the solution turned to an opaque yellow mixture and was stirred for 20 min. 4-Bromoaniline (12.83 g, 74.6 mmol) was added, the solution turned to a clear light brown and the gummy catalyst dissolved further. The mixture was stirred for 16 h. The two reaction mixtures were combined and loaded on to a 1.5 kg Isco silica Redisep column. The column was eluted with DCM/methanol (0%→0.5%, 19 CV). The clean, product containing fractions were evaporated to a pale brown oil. The mixture was dried in a vaccum oven overnight at 40° C. to give 1-methylethyl {(3S)-3-[(4-bromophenyl)amino]butanoyl}carbamate as a white solid (24.2 g, 67% overall).

LCMS (Method C), Rt 0.91, MH+ 343. ee=92%.

Intermediate 4

1-Methylethyl (2E)-2-butenoylcarbamate

Isopropyl carbamate (30 g, 291 mmol, available from TCI) was charged to a 3 L Lara vessel and dry THF (150 ml) added. (2E)-2-Butenoyl chloride (31.2 ml, 326 mmol, available from Aldrich) was added under nitrogen and the jacket cooled to −30° C. When the solution temperature reached −17° C. lithium tert-butoxide (1M, 655 ml, 655 mmol) was added by peristaltic pump over 2 h, keeping the reaction temperature between −10° C. and −18° C. Once the addition was complete the mixture was stirred for 30 min and brought to 0° C. Diethyl ether (450 ml) and hydrochloric acid (1M, 375 ml) were added and the mixture brought to 20° C. with vigorous stirring. The stirring was stopped, the layers allowed to separate and the aqueous layer run off. Brine (375 ml) was added and the mixture stirred vigourously. The stirring was stopped, the layers allowed to separate and the aqueous layer run off. The organic layer was dried ($MgSO_4$), filtered and evaporated to a brown oil (60 g). The oil was applied to a silica column (40+M Biotage) and eluted with DCM/ethyl acetate (1:1 to 0:1, 10 CV). The product containing fractions were evaporated to dryness and loaded on to a silica column (1500 g, Redisep Isco) and eluted with a ethyl acetate in cyclohexane gradient (0-40%). The clean, product containing fractions were evaporated to an off-white solid (15.41 g). LCMS (Method C), Rt 0.68, MH+ 172

Intermediate 5

(R-BINAP)ditriflatebis(acetonitrile)palladium(II)

R-(+)-BINAP (6.08 g, 9.76 mmol, available from Avocado) was stirred in DCM (626 ml) and dichlorobis(acetonitrile)palladium (II) (2.5 g, 9.64 mmol, available from Aldrich) added. The mixture was stirred under nitrogen for 30 min, the suspension had not become a solution and more DCM (100 ml) was added. The mixture was stirred for a further 30 min and silver triflate (5.00 g, 19.47 mmol, available from Aldrich) dissolved in acetonitrile (250 ml) was added. The mixture changed from an orange cloudy suspension to a yellow suspension. The mixture was stirred for 1 h, filtered through Celite™ and evaporated to an orange solid. The residue was dried under vacuum (at approximately 14 mbar) at room temperature over the weekend to give the desired product (10.69 g).

1H NMR (400 MHz, MeCN-d3) δ ppm 2.0 (s, 6H), 6.7 (d, 2H), 6.9 (br m, 4H), 7.1 (br t, 2H), 7.2 (t, 2H), 7.5-7.9 (m, 22H)

Intermediate 6

6-(((2S,4R)-1-Acetyl-6-bromo-2-methyl-1,2,3,4-tetrahydroquinolin-4-yl)amino)nicotinonitrile

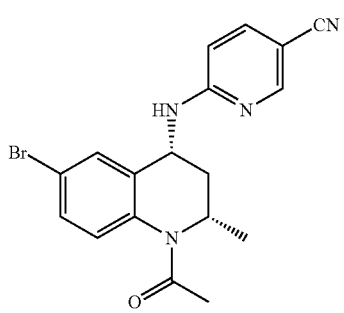 [SMILES: CC(=O)N1c2ccc(Br)cc2[C@H](Nc2ccc(C#N)cn2)C[C@@H]1C]

To a mixture of 1-((2S,4R)-4-amino-6-bromo-2-methyl-3,4-dihydroquinolin-1(2H)-yl)ethanone (for a preparation see Intermediate 7) (2.28 g, 8.05 mmol) and 6-chloronicotinonitrile (2.231 g, 16.10 mmol) was added NMP (20 ml) and the mixture treated with DIPEA (4.22 ml, 24.16 mmol). The mixture was split between 2 flasks and each flask was flushed with nitrogen, sealed and stirred under microwave irradiation at 200° C. for 2 h. The reaction mixtures were combined and partitioned between water and ethyl acetate. The aqueous layer was extracted with ethyl acetate (×4) and the combined organic layers were washed with water (×3), then brine and were dried (MgSO$_4$) filtered and concentrated in vacuo. The brown solid residue was purified by chromatography (ethyl acetate/hexanes gradient) to give 6-(((2S,4R)-1-acetyl-6-bromo-2-methyl-1,2,3,4-tetrahydroquinolin-4-yl)amino)nicotinonitrile (1.940 g, 5.04 mmol, 62.5% yield) as a pale yellow foam. LCMS (HpH), Rt 1.02 min, MH+=386 (1 Br).

Intermediate 6, Alternative Preparation 6-(((2S,4R)-1-acetyl-6-bromo-2-methyl-1,2,3,4-tetrahydroquinolin-4-yl)amino)nicotinonitrile 1-((2S,4R)-4-amino-6-bromo-2-methyl-3,4-dihydroquinolin-1(2H)-yl)ethanone (for a preparation, see Intermediate 7) (18 g, 63.6 mmol) was dissolved in dry NMP (90 mL). 6-chloronicotinonitrile (13.21 g, 95 mmol) and DIPEA (22.20 ml, 127 mmol) were added, the mixture was stirred at 150° C. under a nitrogen atmosphere for 8 h, then allowed to stand overnight at room temperature. The solution was added to water (1 L) and the mixture extracted with EtOAc (2×400 mL). The organic layer was washed with water (2×500 mL), dried and evaporated in vacuo to give a brown foam. This brown foam was purified by silica gel column chromatography (750 g column, eluting with 0-100% EtOAc/cyclohexane). The appropriate fractions were combined and evaporated in vacuo to give 6-(((2S,4R)-1-acetyl-6-bromo-2-methyl-1,2,3,4-tetrahydroquinolin-4-yl)amino) nicotinonitrile (18.7 g, 48.5 mmol, 76% yield) as a pale yellow solid.

LCMS (formate): Rt 0.99 min, MH+ 385/387.

Intermediate 7

1-((2S,4R)-4-Amino-6-bromo-2-methyl-3,4-dihydroquinolin-1(2H)-yl)ethanone

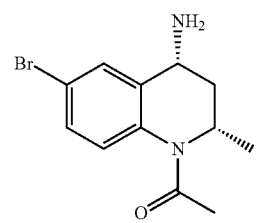 [SMILES: CC(=O)N1c2ccc(Br)cc2[C@H](N)C[C@@H]1C]

A suspension of aluminium chloride (41.2 g, 309 mmol) in DCM (480 ml) at 0° C. under nitrogen was treated with a solution of 1-methylethyl ((2S,4R)-1-acetyl-6-bromo-2-methyl-1,2,3,4-tetrahydroquinolin-4-yl)carbamate (for a preparation see Intermediate 1) (30 g, 81 mmol) in DCM (80 ml) via cannula and the resulting mixture was stirred at this temperature for 30 min. The reaction mixture was then slowly treated with a mixture of triethylamine (136 ml, 975 mmol) and methanol (48 ml) via cannula. The resulting cake formed was stirred in ethyl acetate (800 ml), isolated by filtration and subsequently partitioned between DCM (800 ml) and saturated aqueous sodium hydrogen carbonate solution (800 ml). Sodium potassium tartrate (300 g) was added and the resulting mixture was stirred vigorously for 2 h. The layers were separated and the DCM layer was filtered through a sinter funnel. The filtrate was dried (MgSO$_4$) and concentrated in vacuo to give a first crop of 1-((2S,4R)-4-amino-6-bromo-2-methyl-3,4-dihydroquinolin-1(2H)-yl)ethanone (19.6 g, 69.2 mmol, 85% yield) as a yellow foam. The aqueous phase was treated further with DCM (800 ml) and the biphasic mixture stirred overnight. The layers were then separated and the organic layer was dried over (MgSO$_4$) and concentrated in vacuo to give a second crop of 1-((2S,4R)-4-amino-6-bromo-2-methyl-3,4-dihydroquinolin-1(2H)-yl)ethanone (3.4 g, 12.01 mmol, 14.78% yield). LCMS (HpH), Rt 0.77 min, MH+ 283 (1 Br).

Intermediate 7, Alternative Preparation 1-((2S,4R)-4-amino-6-bromo-2-methyl-3,4-dihydroquinolin-1(2H)-yl)ethanone Aluminium trichloride (31.6 g, 237 mmol) was suspended in DCM (320 mL) and cooled in an ice-bath. A solution of 1-methylethyl ((2S,4R)-1-acetyl-6-bromo-2-methyl-1,2,3,4-tetrahydroquinolin-4-yl)carbamate (for a preparation, see Intermediate 1) (25 g, 67.7 mmol) in DCM (100 mL) was added dropwise over approximately 45 mins and the mixture was left to stir in the ice-bath for a further 1 h. The reaction mixture was quenched by dropwise addition of NaOH (28.4 g, 711 mmol) in water (350 mL), resulting in the formation of a thick precipitate which was broken up to ensure stirring continued. A solution of potassium sodium tartrate (100 g, 354 mmol) in water (400 mL) was added and the mixture stirred overnight. The organic layer was separated and the aqueous layer was further extracted with DCM (2×200 mL). The combined organic layers were dried (Na₂SO₄), filtered and concentrated to give 1-((2S,4R)-4-amino-6-bromo-2-methyl-3,4-dihydroquinolin-1(2H)-yl)ethanone (20.71 g, 65.8 mmol, 97% yield) as a sticky brown oil.

LCMS (formate): Rt 0.49 min, MH+ 266/268.

Intermediate 8

6-(((2S,4R)-1-acetyl-2-methyl-6-(1H-1,2,3-triazol-4-yl)-1,2,3,4-tetrahydroquinolin-4-yl)amino)nicotinonitrile

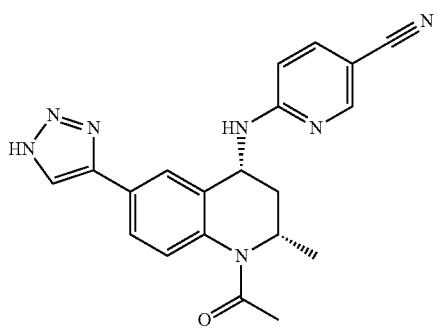 [SMILES: CC(=O)N1c2ccc(-c3c[nH]nn3)cc2[C@H](Nc2ccc(C#N)cn2)C[C@@H]1C]

A microwaveable vial was charged with 6-(((2S,4R)-1-acetyl-6-ethynyl-2-methyl-1,2,3,4-tetrahydroquinolin-4-yl)amino)nicotinonitrile (for a preparation see Intermediate 9) (527 mg, 1.595 mmol), Copper (I) Iodide (30 mg, 0.158 mmol), methanol (0.333 ml), DMF (3 ml). Azidotrimethylsilane (0.423 ml, 3.19 mmol) was added to the solution, the vial sealed and heated at 100° C. for 1 h (microwave). Azidotrimethylsilane (0.211 ml, 1.59 mmol) was added to the vial and the mixture heated for a further 1 h (sealed vial, microwave). Azidotrimethylsilane (0.211 ml, 1.590 mmol), and copper (I) iodide (30 mg, 0.158 mmol) was added. The vial was resealed and heated for a further 1 h. The reaction solution was concentrated in vacuo, diluted with water (15 ml) and extracted with DCM (3×10 ml). The organics were combined and dried (hydrophobic frit). The mixture was concentrated and the sample purified by chromatography on a silica cartridge (50 g) eluting with a methanol/DCM gradient (0-10%). The appropriate fractions were combined and the solvent evaporated in vacuo to give 6-(((2S,4R)-1-acetyl-2-methyl-6-(1H-1,2,3-triazol-4-yl)-1,2,3,4-tetrahydroquinolin-4-yl)amino)nicotinonitrile (50 mg). LCMS (formate): Rt 0.71 min, MH+ 374

Intermediate 9

6-(((2S,4R)-1-acetyl-6-ethynyl-2-methyl-1,2,3,4-tetrahydroquinolin-4-yl)amino)nicotinonitrile

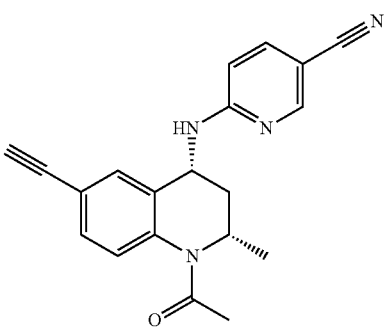 [SMILES: C#Cc1ccc2c(c1)[C@H](Nc1ccc(C#N)cn1)C[C@H](C)N2C(C)=O]

6-(((2S,4R)-1-Acetyl-2-methyl-6-((trimethylsilyl)ethynyl)-1,2,3,4-tetrahydroquinolin-4-yl)amino)nicotinonitrile (for a preparation see Intermediate 10) (1.69 g, 4.20 mmol) was treated with tetrabutylammonium fluoride (1M in THF, 4.62 ml, 4.62 mmol) and THF (18 ml) and the solution stirred at ambient conditions for 30 min. The reaction was concentrated in vacuo, diluted with water (25 ml) and extracted with DCM (3×30 ml). The organics were combined, being dried (hydrophobic frit) and the solvent evaporated in vacuo. The residue was purified by chromatography on a silica cartridge (100 g) eluting with an ethyl acetate/cyclohexane gradient (0-75%). The appropriate fractions were collected and the solvent evaporated in vacuo to give 6-(((2S,4R)-1-acetyl-6-ethynyl-2-methyl-1,2,3,4-tetrahydroquinolin-4-yl)amino) nicotinonitrile (990 mg) as a yellow foam. LCMS (formate), Rt 0.92 min, MH+ 331.

Intermediate 10

6-(((2S,4R)-1-Acetyl-2-methyl-6-((trimethylsilyl)ethynyl)-1,2,3,4-tetrahydroquinolin-4-yl)amino)nicotinonitrile

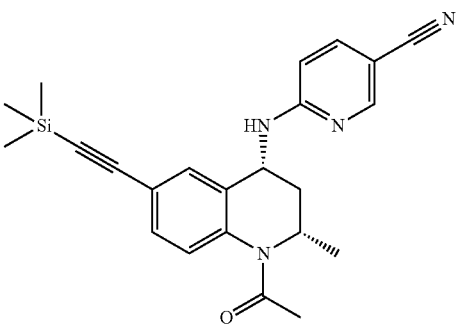 [SMILES: CC(=O)N1c2ccc(C#C[Si](C)(C)C)cc2[C@H](Nc2ccc(C#N)cn2)C[C@@H]1C]

6-(((2S,4R)-1-Acetyl-6-bromo-2-methyl-1,2,3,4-tetrahydroquinolin-4-yl)amino)nicotinonitrile (for a preparation see Intermediate 6) (1.62 g, 4.20 mmol), ethynyltrimethylsilane (17.5 ml, 124 mmol), triethylamine (23 ml, 165 mmol), bis(triphenylphosphine)palladium(II) chloride (0.590 g, 0.841 mmol) and copper(I) iodide (0.080 g, 0.420 mmol) were mixed in DMF (18 ml) and heated at 90° C. overnight. The reaction was concentrated in vacuo, diluted with water (30 ml), and extracted with DCM (3×30 ml). The organics were combined and dried (hydrophobic frit). The solution was concentrated in vacuo, and the residue purified by chromatography on a silica cartridge (100 g) eluting with an ethylacetate/cyclohexane gradient (0-75% over 14 CVs). The appropriate fractions were collected and the solvent evaporated in vacuo to give 6-(((2S,4R)-1-acetyl-2-methyl-6-((trimethylsilyl)ethynyl)-1,2,3,4-tetrahydroquinolin-4-yl)amino)nicotinonitrile (881 mg) as a black foam, which was used without further purification. LCMS (formate), Rt 1.24 min, MH+ 402

Intermediate 11

1-((2S,4R)-4-amino-6-(1-(2-methoxyethyl)-1H-pyrazol-4-yl)-2-methyl-3,4-dihydroquinolin-1(2H)-yl)ethanone

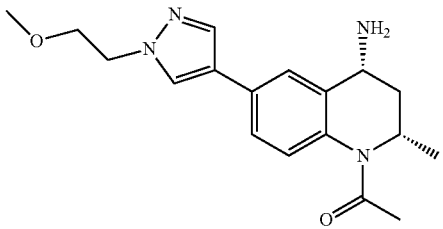

(2S,4R)-1-Acetyl-6-bromo-2-methyl-1,2,3,4-tetrahydro-4-quinolinamine (for a preparation see Intermediate 7) (900 mg, 2.82 mmol), 1-(2-methoxyethyl)-4-(4,4,5,5-tetramethyl-1,3,2-dioxaborolan-2-yl)-1H-pyrazole (852 mg, 3.38 mmol), [1,1'-bis(diphenylphosphino)ferrocene]dichloropalladium (II) (309 mg, 0.422 mmol) and K$_2$CO$_3$ (895 mg, 6.48 mmol) were combined in 1,4-dioxane (12 ml) and water (4.0 ml) and heated at 110° C. for 60 min (microwave). The reaction was heated for a further 10 min and then, for a further 30 min under the same conditions. PdCl$_2$(dppf) (309 mg, 0.422 mmol), K$_2$CO$_3$ (895 mg, 6.48 mmol) and water (1.5 ml) were added and the mixture heated at 110° C. for 30 min (microwave). The reaction mixture was partitioned between saturated aqueous sodium hydrogen carbonate (150 ml) and DCM (3×150 ml). The organics were combined, dried (hydrophobic frit) and evaporated under vacuum. The residue was dissolved in DCM, the solution applied to a silica cartridge (100 g) and purified the cartridge eluted with an ethyl acetate/cyclohexane gradient (0-100% over 10 CV followed by 100% ethyl acetate for 5 CV). The cartridge was washed using a methanol/DCM gradient (0-20% over 10 CV, followed by holding at 20% methanol/DCM for 5 CV). The cartridge was further washed using a gradient 2M ammonia in methanol/DCM (0-20% over 10 CV, followed by 2M ammonia in methanol/DCM 20% for 5 CV). The appropriate fractions were combined and evaporated under vacuum to leave 1-((2S,4R)-4-amino-6-(1-(2-methoxyethyl)-1H-pyrazol-4-yl)-2-methyl-3,4-dihydroquinolin-1(2H)-yl)ethanone (631 mg, 1.921 mmol, 68% yield) as a brown glass. LCMS (HpH), Rt 0.68 min, MH+ 329

Example 1

1-methylethyl ((2S,4R)-1-acetyl-2-methyl-6-{1-[2-(methyloxy)ethyl]-1H-pyrazol-4-yl}-1,2,3,4-tetrahydro-4-quinolinyl)carbamate

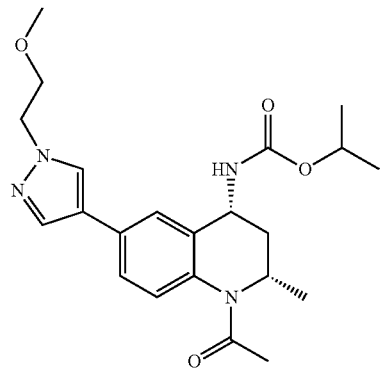 [SMILES: COCCn1cc(-c2ccc3c(c2)[C@H](NC(=O)OC(C)C)C[C@H](C)N3C(C)=O)cn1]

1-Methylethyl [(2S,4R)-1-acetyl-6-bromo-2-methyl-1,2,3,4-tetrahydro-4-quinolinyl]carbamate (for preparation see Intermediate 1) (185 mg), 1-[2-(methyloxy)ethyl]-4-(4,4,5,5-tetramethyl-1,3,2-dioxaborolan-2-yl)-1H-pyrazole (for a preparation see Journal of Heterocyclic Chemistry, 41(6), 931-939; 2004) (151 mg), potassium carbonate (90 mg) and tetrakis(triphenylphosphine)palladium(0) (28.9 mg) were combined in ethanol and toluene under nitrogen and heated to 80° C. for 18 h. The reaction was concentrated, the residue partioned between ethyl acetate (10 ml) and water (10 ml) and the aqueous layer was extracted with ethyl acetate (10 ml). The combined organics were washed with brine (25 ml), dried with sodium sulphate, filtered and concentrated. The residue was purified by MDAP (formate ×2) and the collected product dissolved in 1,4-dioxane (0.5 ml) and cooled in a CO$_2$ bath then left on a freeze dryer overnight. The resulting white solid was dried at 40° C. under vacuum overnight to give 1-methylethyl ((2S,4R)-1-acetyl-2-methyl-6-{1-[2-(methyloxy)ethyl]-1H-pyrazol-4-yl}-1,2,3,4-tetrahydro-4-quinolinyl)carbamate (84.7 mg). LCMS (formate), Rt 0.84 min, MH+ 415

Example 2

6-(((2S,4R)-1-acetyl-6-(1-(2-methoxyethyl)-1H-pyrazol-4-yl)-2-methyl-1,2,3,4-tetrahydroquinolin-4-yl)amino)nicotinonitrile

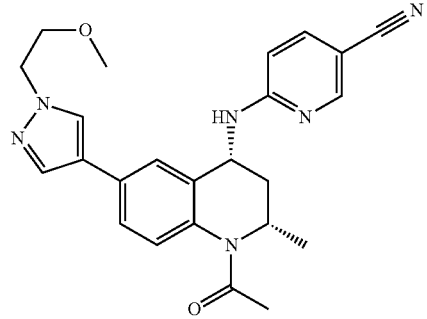 [SMILES: COCCn1cc(-c2ccc3c(c2)[C@H](Nc2ccc(C#N)cn2)C[C@H](C)N3C(C)=O)cn1]

A microwaveable vial was charged with 6-(((2S,4R)-1-acetyl-6-bromo-2-methyl-1,2,3,4-tetrahydroquinolin-4-yl)

amino)nicotinonitrile (for a preparation see Intermediate 6) (74 mg, 0.192 mmol), 1-(2-methoxyethyl)-4-(4,4,5,5-tetramethyl-1,3,2-dioxaborolan-2-yl)-1H-pyrazole (CAS No. 847818-71-7 available from Milestone PharmTech USA Inc.) (63 mg, 0.250 mmol), [1,1'-bis(diphenylphosphino)ferrocene]dichloropalladium(II) (21 mg, 0.029 mmol), potassium carbonate (56 mg, 0.405 mmol), water (0.5 ml), and 1,4-dioxane (1.5 ml). The vial was sealed and heated at 120° C. for 30 min (microwave). The reaction solution was diluted with water (10 ml), extracted with ethyl acetate (3×15 ml). The organics were combined, dried (hydrophobic frit). The solvent was evaporated in vacuo. The residue was dissolved in methanol/DMSO (1:1, 1 ml) and purified by MDAP (TFA). The solvent was evaporated under a stream of nitrogen, the residue was redissolved in methanol and filtered through an aminopropyl SPE (2 g). The solvent was evaporated in vacuo, to give 6-(((2S,4R)-1-acetyl-6-(1-(2-methoxyethyl)-1H-pyrazol-4-yl)-2-methyl-1,2,3,4-tetrahydroquinolin-4-yl)amino)nicotinonitrile (40 mg) as a white solid.

LCMS (formate): Rt 0.82 min, MH+ 431.

Example 2

Alternative Preparation 6-(((2S,4R)-1-acetyl-6-(1-(2-methoxyethyl)-1H-pyrazol-4-yl)-2-methyl-1,2,3,4-tetrahydroquinolin-4-yl)amino)nicotinonitrile 6-(((2S,4R)-1-acetyl-6-bromo-2-methyl-1,2,3,4-tetrahydroquinolin-4-yl)amino)nicotinonitrile (Intermediate 6) (10 g, 26.0 mmol), PEPPSI™ (1.764 g, 2.60 mmol), KOH (4.37 g, 78 mmol) and 1-(2-methoxyethyl)-4-(4,4,5,5-tetramethyl-1,3,2-dioxaborolan-2-yl)-1H-pyrazole (CAS No. 847818-71-7 available from Milestone PharmTech USA Inc.) (11.78 g, 46.7 mmol) were combined in a mixture of toluene (80 mL), EtOH (40 mL) and water (50 mL). The mixture was degassed and then heated at reflux under a nitrogen atmosphere for 6 h. The solution was cooled, diluted with EtOAc (200 mL) and washed with water (200 mL). The organic layer was dried over sodium sulphate and concentrated in vacuo to give a pale yellow gum. This yellow gum was purified by silica gel column chromatography (330 g column, eluting with 0-100% EtOAC/cyclohexane followed by 10% MeOH/EtOAc). The appropriate fractions were collected and the solvent evaporated in vacuo to give the crude product which was further purified by preparative HPLC (Method HpH) and then dried overnight in a vacuum oven at 55° C. to give 6-(((2S,4R)-1-acetyl-6-(1-(2-methoxyethyl)-1H-pyrazol-4-yl)-2-methyl-1,2,3,4-tetrahydroquinolin-4-yl)amino)nicotinonitrile (4.62 g).

LCMS (formate): Rt 0.82 min, MH+ 431.

$^1$H NMR (DMSO-d6): 8.42 (d, J=2.6 Hz, 1H), 8.02 (s, 1H), 7.97 (d, J=8.4 Hz, 1H), 7.79 (dd, J=8.8, 2.6 Hz, 1H), 7.76 (s, 1H), 7.48 (dd, J=8.1, 2.2 Hz, 1H), 7.33 (d, J=8.1 Hz, 1H), 7.27 (s, 1H), 6.79 (d, J=8.8 Hz, 1H), 4.99 (br. s., 1H), 4.62-4.77 (m, 1H), 4.26 (t, J=5.3 Hz, 2H), 3.63-3.71 (m, 2H), 3.21 (s, 3H), 2.56 (ddd, J=12.7, 8.3, 4.6 Hz, 1H), 2.09 (s, 3H), 1.24-1.38 (m, 1H), 1.08 (d, J=6.2 Hz, 3H)

Example 3

6-(((2S,4R)-1-acetyl-6-(1-(2-methoxyethyl)-1H-1,2,3-triazol-4-yl)-2-methyl-1,2,3,4-tetrahydroquinolin-4-yl)amino)nicotinonitrile

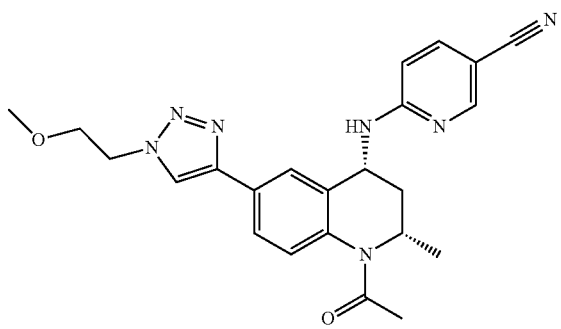 [SMILES: COCCn1cc(-c2ccc3c(c2)[C@H](Nc2ccc(C#N)cn2)C[C@H](C)N3C(C)=O)nn1]

Example 4

6-(((2S,4R)-1-acetyl-6-(2-(2-methoxyethyl)-2H-1,2,3-triazol-4-yl)-2-methyl-1,2,3,4-tetrahydroquinolin-4-yl)amino)nicotinonitrile

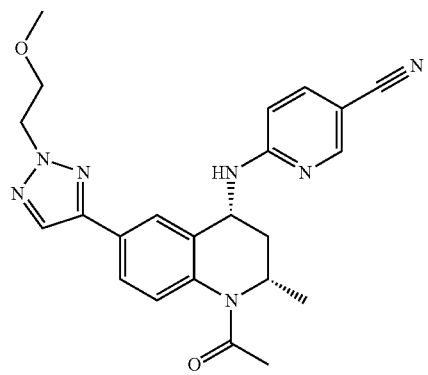 [SMILES: COCCn1ncc(-c2ccc3c(c2)[C@H](Nc2ccc(C#N)cn2)C[C@H](C)N3C(C)=O)n1]

A solution of 6-(((2S,4R)-1-acetyl-2-methyl-6-(1H-1,2,3-triazol-4-yl)-1,2,3,4-tetrahydroquinolin-4-yl)amino)nicotinonitrile (for a preparation see Intermediate 8) (50 mg, 0.134 mmol) in DMF (3 ml) was cooled to 0° C. in an ice-water bath. To the solution was added 1-bromo-2-methoxyethane (0.04 ml, 0.420 mmol) and potassium carbonate (56 mg, 0.405 mmol). The solution was then allowed to warm to room temperature, and was stirred at ambient conditions for 2 h. Sodium iodide (61 mg, 0.407 mmol) was added to the reaction solution and the reaction was stirred at ambient temperature overnight. 1-Bromo-2-methoxyethane (0.013 ml, 0.134 mmol), potassium carbonate (21 mg, 0.152 mmol), and sodium iodide (21 mg, 0.140 mmol) were added to the reaction, which was heated at 60° C. for 1 h. Further portions of 1-bromo-2-methoxyethane (0.013 ml, 0.134 mmol), potassium carbonate (21 mg, 0.152 mmol), and sodium iodide (21 mg, 0.140 mmol) were added to the reaction and heating continued for 3 h. The reaction mixture was concentrated in vacuo, diluted with water (10 ml) and extracted with DCM (3×15 ml). The organics were combined and dried (hydrophobic frit). The solvent was then evaporated in vacuo, the sample redissolved in methanol/DMSO (1:1, 1 ml) and purified by MDAP (formate). Both regiosiomers were collected to give 6-(((2S,4R)-1-acetyl-6-(1-(2-methoxyethyl)-1H-1,2,3-triazol-4-yl)-2-methyl-1,2,3,4-tetrahydroquinolin-4-yl) amino)nicotinonitrile (8 mg) and 6-(((2S,4R)-1-acetyl-6-(2-(2-methoxyethyl)-2H-1,2,3-triazol-4-yl)-2-methyl-1,2,3,4-tetrahydroquinolin-4-yl)amino)nicotinonitrile (18 mg).

6-(((2S,4R)-1-acetyl-6-(1-(2-methoxyethyl)-1H-1,2,3-triazol-4-yl)-2-methyl-1,2,3,4-tetrahydroquinolin-4-yl) amino)nicotinonitrile LCMS (formate), Rt 0.78 min, MH+ 432. 6-(((2S,4R)-1-acetyl-6-(2-(2-methoxyethyl)-2H-1,2,3-triazol-4-yl)-2-methyl-1,2,3,4-tetrahydroquinolin-4-yl) amino)nicotinonitrile LCMS (formate), Rt 0.86 min, MH+ 432.

Example 5

1-((2S,4R)-4-((5-chloropyridin-2-yl)amino)-6-(1-(2-methoxyethyl)-1H-pyrazol-4-yl)-2-methyl-3,4-dihydroquinolin-1(2H)- yl)ethanone

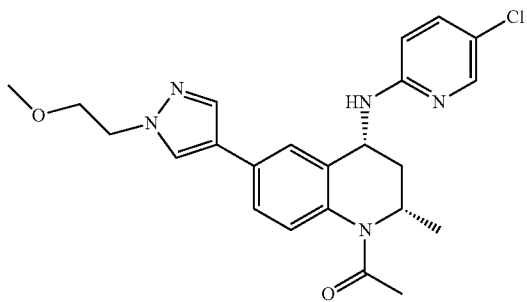 [SMILES: COCCn1cc(-c2ccc3c(c2)[C@H](Nc2ccc(Cl)cn2)C[C@H](C)N3C(C)=O)cn1]

1-((2S,4R)-4-amino-6-(1-(2-methoxyethyl)-1H-pyrazol-4-yl)-2-methyl-3,4-dihydroquinolin-1(2H)-yl)ethanone (for a preparation see Intermediate 11) (100 mg, 0.304 mmol), 2-bromo-5-chloropyridine (117 mg, 0.609 mmol), Davephos (23.97 mg, 0.061 mmol), Pd$_2$(dba)$_3$ (27.9 mg, 0.030 mmol) and sodium tert-butoxide (58.5 mg, 0.609 mmol) were combined in 1,4-dioxane (3 ml) and the mixture degassed over a period of 20 min before being heated at 120° C. for 25 min (microwave). The reaction mixture was partitioned between water (100 ml) and DCM (3×100 ml). The organics were combined, dried (hydrophobic frit) and evaporated under vacuum. The residual brown oil was dissolved in DMSO (2×1 ml) and purified by MDAP (HpH ×2). The solvent was evaporated under vacuum to give 1-((2S,4R)-4-((5-chloropyridin-2-yl)amino)-6-(1-(2-methoxyethyl)-1H-pyrazol-4-yl)-2-methyl-3,4-dihydroquinolin-1(2H)-yl)ethanone (51 mg, 0.116 mmol, 38% yield) as a yellow glass. LCMS (formate), Rt 0.87 min, MH+ 440.

Example 6

1-((2S,4R)-6-(1-(2-methoxyethyl)-1H-pyrazol-4-yl)-2-methyl-4-((5-methylpyridin-2-yl)amino)-3,4-dihydroquinolin-1(2H)- yl)ethanone

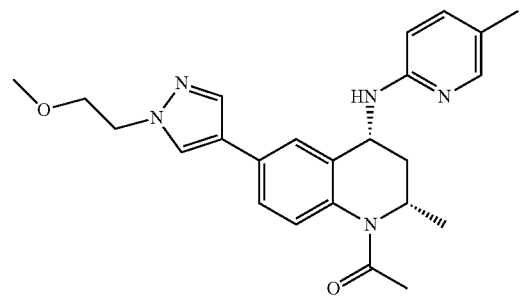

1-((2S,4R)-4-Amino-6-(1-(2-methoxyethyl)-1H-pyrazol-4-yl)-2-methyl-3,4-dihydroquinolin-1(2H)-yl)ethanone (for a preparation see Intermediate 7) (100 mg, 0.304 mmol), 2-bromo-5-methylpyridine (105 mg, 0.609 mmol), Davephos (23.97 mg, 0.061 mmol), Pd$_2$(dba)$_3$ (27.9 mg, 0.030 mmol) and sodium tert-butoxide (58.5 mg, 0.609 mmol) were combined in 1,4-dioxane (3 ml) and the mixture degassed over a period of 20 min. The mixture was heated at 120° C. for 25 min (microwave). The reaction mixture was partitioned between water (100 ml) and DCM (3×100 ml). The organics were combined, dried (hydrophobic frit) and evaporated under vacuum. The residual brown oil was dissolved in DMSO (2×1 ml) and purified by MDAP (HpH ×2). The solvent was evaporated under vacuum to give 1-((2S,4R)-6-(1-(2-methoxyethyl)-1H-pyrazol-4-yl)-2-methyl-4-((5-methylpyridin-2-yl)amino)-3,4-dihydroquinolin-1(2H)-yl) ethanone (49 mg, 0.117 mmol, 38% yield) as a yellow glass. LCMS (formate), Rt 0.61 min, MH+ 420.

Example 7

1-((2S,4R)-4-((3-chlorophenyl)amino)-6-(1-(2-methoxyethyl)-1H-pyrazol-4-yl)-2-methyl-3,4-dihydroquinolin-1(2H)-yl)ethanone

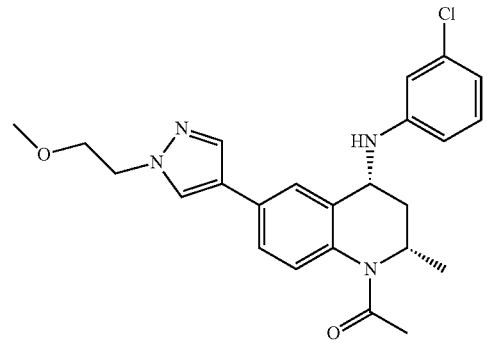 [SMILES: COCCn1cc(-c2ccc3c(c2)[C@H](Nc2cccc(Cl)c2)C[C@H](C)N3C(C)=O)cn1]

1-((2S,4R)-4-Amino-6-(1-(2-methoxyethyl)-1H-pyrazol-4-yl)-2-methyl-3,4-dihydroquinolin-1(2H)-yl)ethanone (for a preparation see Intermediate 7) (100 mg, 0.304 mmol), 1-bromo-3-chlorobenzene (0.072 ml, 0.609 mmol), Davephos (24 mg, 0.061 mmol), Pd$_2$(dba)$_3$ (27.9 mg, 0.030 mmol) and sodium tert-butoxide (58.5 mg, 0.609 mmol) were combined in 1,4-dioxane (3 ml) and the mixture degassed over a period of 20 min. The mixture was heated at 120° C. for 25 min (microwave). The reaction mixture was partitioned between water (100 ml) and DCM (3×100 ml). The organics were combined, dried (hydrophobic frit) and evaporated under vacuum. The residual brown oil dissolved in DMSO (2×1 ml) and purified by MDAP (formate ×2). The solvent was evaporated under vacuum, the residue dissolved in DCM and applied to a silica cartridge (10 g). The cartridge was eluted with an ethyl acetate/cyclohexane gradient (0-100% over 10 CV followed by holding at 100% ethyl acetate for 5 CV). The appropriate fractions were combined and evaporated under vacuum to give 1-((2S,4R)-4-((3-chlorophenyl) amino)-6-(1-(2-methoxyethyl)-1H-pyrazol-4-yl)-2-methyl-3,4-dihydroquinolin-1(2H)-yl)ethanone (39 mg, 0.089 mmol, 29% yield) as a colourless glass. LCMS (formate), Rt 1.05 min, MH+ 438.

Example 8

1-((2S,4R)-6-(1-(2-methoxyethyl)-1H-pyrazol-4-yl)-2-methyl-4-((5-methylpyrazin-2-yl)amino)-3,4-dihydroquinolin-1(2H)-yl)ethanone

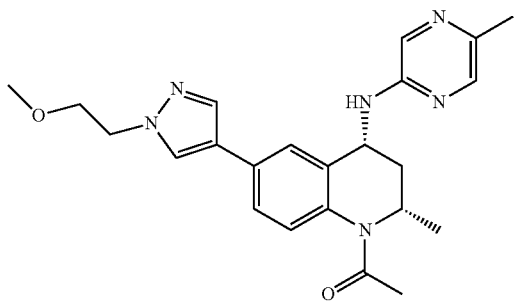

1-((2S,4R)-4-Amino-6-(1-(2-methoxyethyl)-1H-pyrazol-4-yl)-2-methyl-3,4-dihydroquinolin-1(2H)-yl)ethanone (for a preparation see Intermediate 7) (150 mg, 0.457 mmol), 2-chloro-5-methylpyrazine (147 mg, 1.142 mmol), Davephos (71.9 mg, 0.183 mmol), Pd$_2$(dba)$_3$ (84 mg, 0.091 mmol) and sodium tert-butoxide (132 mg, 1.370 mmol) were combined in 1,4-dioxane (4 ml) and the mixture heated at 120° C. for 25 min (microwave). The reaction mixture was partitioned between water (75 ml) and DCM (3×75 ml). The organics were combined, dried (hydrophobic frit) and evaporated under vacuum. The resulting brown oil was dissolved in DMSO (3×1 ml) and purified by MDAP (formate ×3). The solvent was evaporated under vacuum to give 1-((2S,4R)-6-(1-(2-methoxyethyl)-1H-pyrazol-4-yl)-2-methyl-4-((5-methylpyrazin-2-yl)amino)-3,4-dihydroquinolin-1(2H)-yl) ethanone (91 mg, 0.216 mmol, 47% yield) as a yellow glass. LCMS (formate), Rt 0.75 min, MH+ 421.

Reference Compound A: 2-methyl-6-(methyloxy)-4H-3,1-benzoxazin-4-one

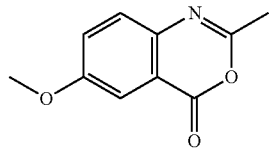

A solution of 5-methoxyanthranilic acid (Lancaster) (41.8 g, 0.25 mol) was refluxed in acetic anhydride (230 ml) for 3.5 h before being concentrated under reduced pressure. The crude compound was then concentrated twice in the presence of toluene before being filtered and washed twice with ether to yield to the title compound (33.7 g, 71% yield) as a brown solid; LC/MS (Method D): m/z 192 [M+H]$^+$, Rt 1.69 min.

Reference Compound B: [2-amino-5-(methyloxy) phenyl](4-chlorophenyl)methanone

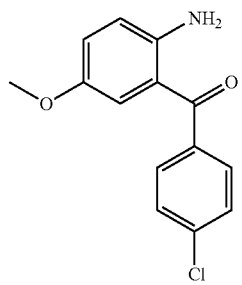 [SMILES: COc1ccc(N)c(C(=O)c2ccc(Cl)cc2)c1]

To a solution of 2-methyl-6-(methyloxy)-4H-3,1-benzoxazin-4-one (for a preparation see Reference compound A) (40.0 g, 0.21 mol) in a toluene/ether (2/1) mixture (760 ml) at 0° C. was added dropwise a solution of 4-chlorophenylmagnesium bromide (170 ml, 1M in diethyl ether, 0.17 mol). The reaction mixture was allowed to warm to room temperature and stirred for 1 h before being quenched with 1N HCl (200 ml). The aqueous layer was extracted with EtOAc (3×150 ml) and the combined organics were washed with brine (100 ml), dried over Na$_2$SO$_4$, filtered and concentrated under reduced pressure. The crude compound was then dissolved in ethanol (400 ml) and 6N HCl (160 ml) was added. The reaction mixture was refluxed for 2 h before being concentrated to one-third in volume. The resulting solid was filtered and washed twice with ether before being suspended in EtOAc and neutralised with 1N sodium hydroxide. The aqueous layer was extracted with EtOAc (3×150 ml) and the combined organics were washed with brine (150 ml), dried over Na$_2$SO$_4$, filtered and concentrated under reduced pressure.

The title compound was obtained as a yellow solid (39 g, 88% yield) LC/MS (Method D): m/z 262 [M+H]+, Rt 2.57 min.

Reference Compound C: Methyl $N^1$-[2-[(4-chlorophenyl)carbonyl]-4-(methyloxy)phenyl]-$N^2$-{[(9H-fluoren-9-ylmethyl)oxy]carbonyl}-L-α-asparaginate

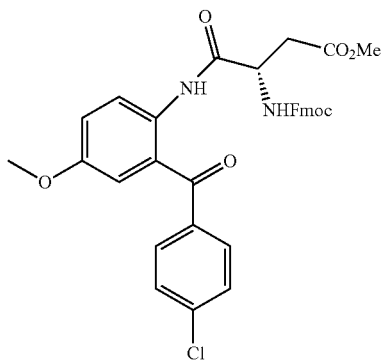

Methyl N-{[(9H-fluoren-9-ylmethyl)oxy]carbonyl}-L-α-aspartyl chloride (*Int. J. Peptide Protein Res.* 1992, 40, 13-18) (93 g, 0.24 mol) was dissolved in CHCl₃ (270 ml) and [2-amino-5-(methyloxy)phenyl](4-chlorophenyl)methanone (for a preparation see Reference compound B) (53 g, 0.2 mol) was added. The resulting mixture was stirred at 60° C. for 1 h before being cooled and concentrated at 60% in volume. Ether was added at 0° C. and the resulting precipitate was filtered and discarded. The filtrate was concentrated under reduced pressure and used without further purification.

Reference Compound D: Methyl [(3S)-5-(4-chlorophenyl)-7-(methyloxy)-2-oxo-2,3-dihydro-1H-1,4-benzodiazepin-3-yl]acetate

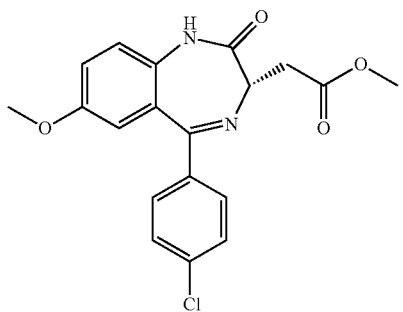

To a solution of methyl N1-[2-[(4-chlorophenyl)carbonyl]-4-(methyloxy)phenyl]-N2-{[(9H-fluoren-9-ylmethyl)oxy]carbonyl}-L-α-asparaginate (for a preparation see Reference compound C) (assumed 0.2 mol) in DCM (500 ml) was added Et₃N (500 ml, 3.65 mol) and the resulting mixture was refluxed for 24 h before being concentrated. The resulting crude amine was dissolved in 1,2-DCE (1.5 L) and AcOH (104 ml, 1.8 mol) was added carefully. The reaction mixture was then stirred at 60° C. for 2 h before being concentrated in vacuo and dissolved in DCM. The organic layer was washed with 1N HCl and the aqueous layer was extracted with DCM (×3). The combined organic layers were washed twice with water, and brine, dried over Na₂SO₄, filtered and concentrated under reduced pressure. The crude solid was recrystallised in MeCN leading to the title compound (51 g) as a pale yellow solid. The filtrate could be concentrated and recrystallised in MeCN to give to another 10 g of the desired product $R_f$=0.34 (DCM/MeOH: 95/5).

HRMS MH+ calculated for $C_{19}H_{18}{}^{35}ClN_2O_4$ 373.0955. found 373.0957.

Reference Compound E: Methyl [(3S)-5-(4-chlorophenyl)-7-(methyloxy)-2-thioxo-2,3-dihydro-1H-1,4-benzodiazepin-3-yl]acetate

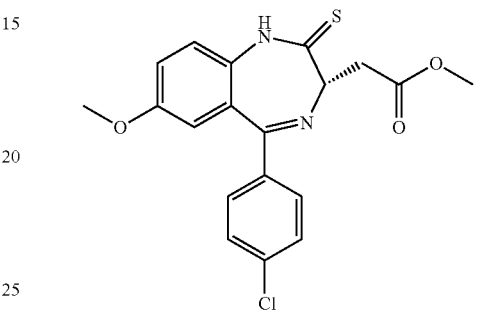

A suspension of $P_4S_{10}$ (36.1 g, 81.1 mmol) and Na₂CO₃ (8.6 g, 81.1 mmol) in 1,2-DCE (700 ml) at room temperature was stirred for 2 h before methyl [(3S)-5-(4-chlorophenyl)-7-(methyloxy)-2-oxo-2,3-dihydro-1H-1,4-benzodiazepin-3-yl]acetate (for a preparation see Reference compound D) (16.8 g, 45.1 mmol) was added. The resulting mixture was stirred at 70° C. for 2 h before being cooled and filtered. The solid was washed twice with DCM and the filtrate washed with sat. Sodium hydrogen carbonate and brine. The organic layer was dried over Na₂SO₄, filtered and concentrated under reduced pressure. The crude product was purified by flash-chromatography on silica gel (DCM/MeOH: 99/1) to afford the title compound (17.2 g, 98% yield) as a yellowish solid. LC/MS (Method D): m/z 389 [M($^{35}$Cl)+H]⁺, Rt 2.64 min HRMS MH+ calculated for $C_{19}H_{18}{}^{35}ClN_2O_3S$ 389.0727. found 389.0714.

Reference Compound F: Methyl [(3S)-2-[(1Z)-2-acetylhydrazino]-5-(4-chlorophenyl)-7-(methyloxy)-3H-1,4-benzodiazepin-3-yl]acetate

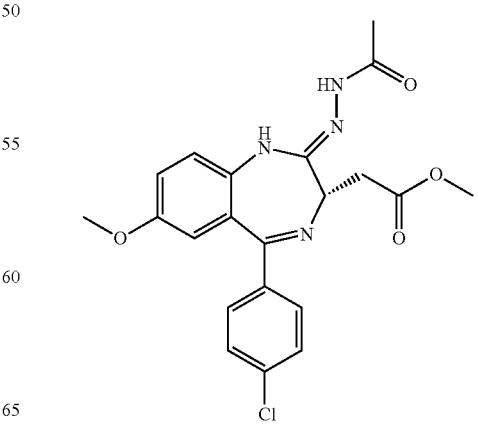

To a suspension of methyl [(3S)-5-(4-chlorophenyl)-7-(methyloxy)-2-thioxo-2,3-dihydro-1H-1,4-benzodiazepin-3-yl]acetate (for a preparation see Reference compound E (9.0 g, 23.2 mmol) in THF (300 ml) at 0° C. was added hydrazine monohydrate (3.4 ml, 69.6 mmol) dropwise. The reaction mixture was stirred for 5 h between 5° C. and 15° C. before being cooled at 0° C. Et₃N (9.7 ml, 69.6 mmol) was then added slowly and acetyl chloride (7.95 ml, 69.6 mmol) was added dropwise. The mixture was then allowed to warm to room temperature for 16 h before being concentrated under reduced pressure. The crude product was dissolved in DCM and washed with water. The organic layer was dried over Na₂SO₄, filtered and concentrated in vacuo to give the crude title compound (9.7 g, 98% yield) which was used without further purification. R$_f$=0.49 (DCM/MeOH: 90/10).

Reference Compound G: Methyl [(4S)-6-(4-chlorophenyl)-1-methyl-8-(methyloxy)-4H-[1,2,4]triazolo[4,3-a][1,4]benzodiazepin-4-yl]acetate

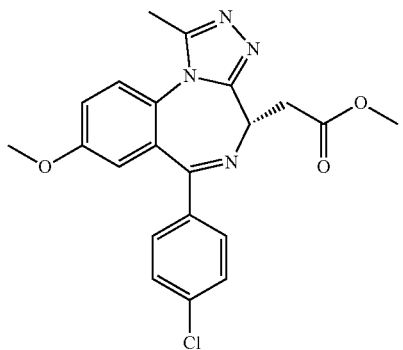

The crude methyl [(3S)-2-[(1Z)-2-acetylhydrazino]-5-(4-chlorophenyl)-7-(methyloxy)-3H-1,4-benzodiazepin-3-yl]acetate (for a preparation see Reference compound F) (assumed 9.7 g) was suspended in THF (100 ml) and AcOH (60 ml) was added at room temperature. The reaction mixture was stirred at this temperature for 2 days before being concentrated under reduced pressure. The crude solid was triturated in i-Pr₂O and filtered to give the title compound (8.7 g, 91% over 3 steps) as an off-white solid.

HRMS MH+ calculated for C₂₁H₂₀ClN₄O₃ 411.1229. found 411.1245.

Reference Compound H: [(4S)-6-(4-Chlorophenyl)-1-methyl-8-(methyloxy)-4H-[1,2,4]triazolo[4,3-a][1,4]benzodiazepin-4-yl]acetic acid

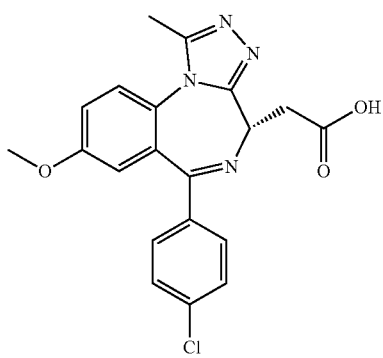 [SMILES: COc1ccc2c(c1)C(c1ccc(Cl)cc1)=N[C@@H](CC(=O)O)c1nnc(C)n1-2]

To a solution of methyl [(4S)-6-(4-chlorophenyl)-1-methyl-8-(methyloxy)-4H-[1,2,4]triazolo[4,3-a][1,4]benzodiazepin-4-yl]acetate (for a preparation see Reference compound G) (7.4 g, 18.1 mmol) in THF (130 ml) at room temperature was added 1N sodium hydroxide (36.2 ml, 36.2 mmol). The reaction mixture was stirred at this temperature for 5 h before being quenched with 1N HCl (36.2 ml) and concentrated in vacuo. Water is then added and the aqueous layer was extracted with DCM (×3) and the combined organic layers were dried over Na₂SO₄, filtered and concentrated under reduced pressure to give the title compound (7 g, 98% yield) as a pale yellow solid.

Reference Compound H: 1,1-dimethylethyl [5-({[(4S)-6-(4-chlorophenyl)-1-methyl-8-(methyloxy)-4H-[1,2,4]triazolo[4,3-a][1,4]benzodiazepin-4-yl]acetyl}amino)pentyl]carbamate

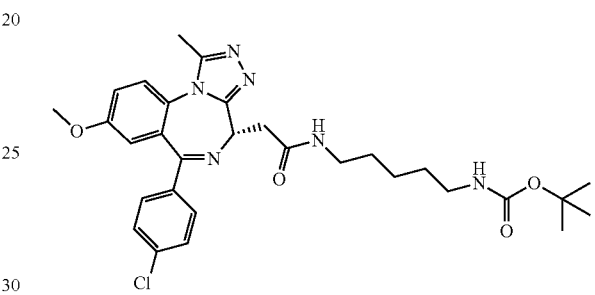

A mixture of [(4S)-6-(4-chlorophenyl)-1-methyl-8-(methyloxy)-4H-[1,2,4]triazolo[4,3-a][1,4]benzodiazepin-4-yl]acetic acid (for a preparation see Reference compound G) (1.0 g, 2.5 mmol), HATU (1.9 g, 5 mmol) and DIPEA (0.88 ml, 5 mmol) was stirred for 80 minutes at room temperature, to this was added 1,1-dimethylethyl (4-aminobutyl)carbamate (1.05 ml, 5.0 mmol, available from Aldrich). The reaction mixture was stirred at room temperature for 2 h before it was concentrated. The residue was taken up in dichloromethane and washed with 1N HCl. The aqueous layer was extracted with dichloromethane twice. Organic layer was washed with 1N sodium hydroxide, followed by a saturated solution of sodium chloride, dried over sodium sulphate and concentrated. The residue was purified by flash-chromatography on silica using dichloromethane/methanol 95/5 to give the title compound as a yellow solid (1.2 g). LC/MS (Method D): rt=3.04 min.

Reference Compound J: N-(5-aminopentyl)-2-[(4S)-6-(4-chlorophenyl)-1-methyl-8-(methyloxy)-4H-[1,2,4]triazolo[4,3-a][1,4]benzodiazepin-4-yl]acetamide trifluoroacetate

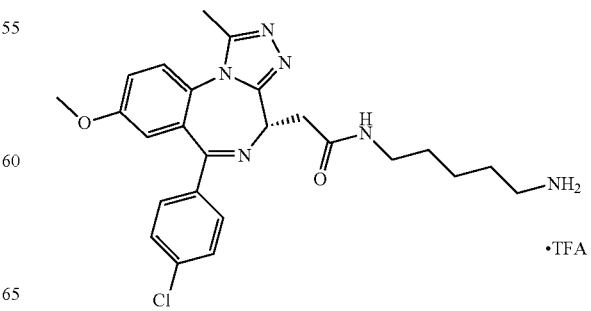

To a solution of 1,1-dimethylethyl [5-({[(4S)-6-(4-chlorophenyl)-1-methyl-8-(methyloxy)-4H-[1,2,4]triazolo[4,3-a][1,4]benzodiazepin-4-yl]acetyl}amino)pentyl]carbamate (for a preparation see Reference compound H) (0.2 g, 0.34 mmol) in dichloromethane (3 ml) was added trifluoroacetic acid (0.053 ml, 0.68 mmol) dropwise at 0° C. The reaction mixture was stirred for 3 h from 0° C. to room temperature. The reaction mixture was concentrated to dryness to afford the title compound as a hygroscopic yellow oil (200 mg)

LC/MS (Method D): rt=2.33 min.

HRMS MH+ calculated for $C_{25}H_{29}ClN_6O_2$ 481.2119. found 481.2162.

Reference Compound K: Mixture of 5- and 6-isomers of Alexa Fluor 488-N-(5-aminopentyl)-2-[(4S)-6-(4-chlorophenyl)-1-methyl-8-(methyloxy)-4H-[1,2,4]triazolo[4,3-a][1,4]benzodiazepin-4-yl]acetamide N-(5-aminopentyl)-2-[(4S)-6-(4-chlorophenyl)-1-methyl-8-(methyloxy)-4H-[1,2,4]triazolo[4,3-a][1,4]benzodiazepin-4-yl]acetamide trifluoroacetate (for a preparation see Reference compound J) (7.65 mg, 0.013 mmol) was dissolved in N,N-dimethylformamide (DMF) (300 μl) and added to Alexa Fluor 488 carboxylic acid succinimidyl ester (5 mg, 7.77 μmol, mixture of 5 and 6 isomers, available from Invitrogen, product number A-20100) in an Eppendorf centrifuge tube. Hunig's base (7.0 μl, 0.040 mmol) was added and the mixture vortex mixed overnight. After 18 h the reaction mixture was evaporated to dryness and the residue redissolved in DMSO/water (50%, <1 ml total), applied to a preparative Phenomenex Jupiter C18 column and eluted with a gradient of 95% A: 5% B to 100% B (A=0.1% trifluoroacetic acid in water, B=0.1% TFA/90% acetonitrile/10% water) at a flow rate of 10 ml/min over 150 minutes. Impure fractions were combined and re-purified using the same system. Fractions were combined and evaporated to yield the title product (2.8

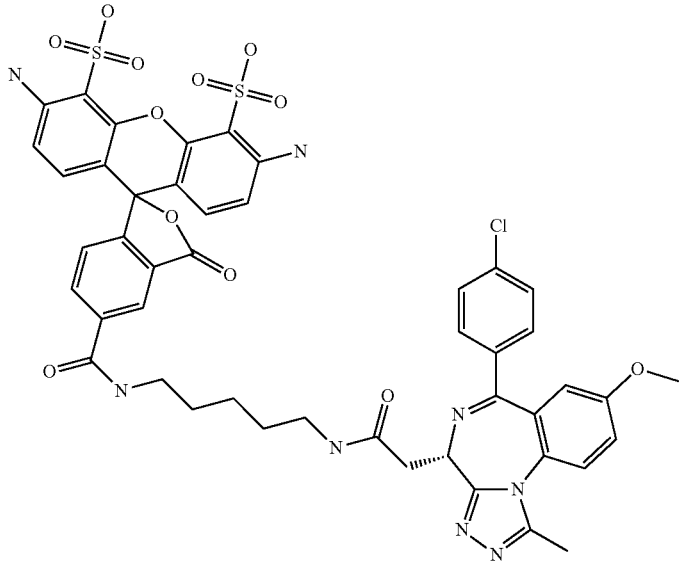

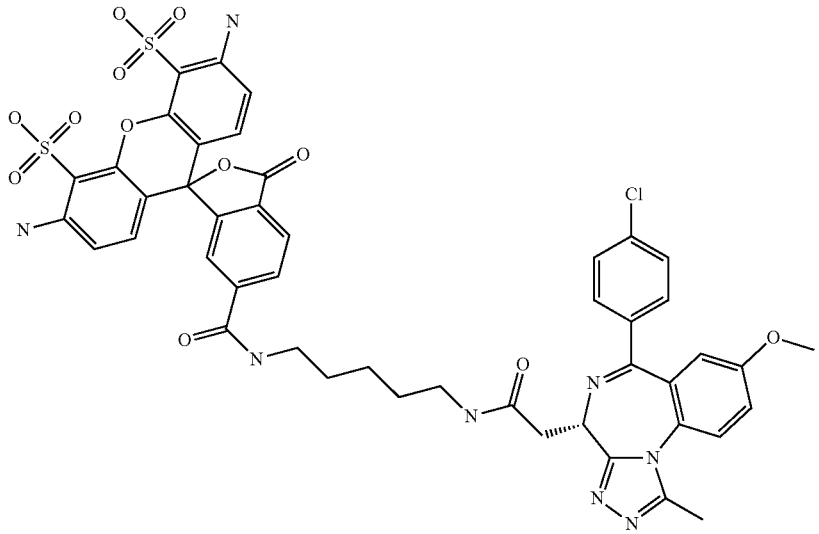

mg) as a mixture of the 2 regioisomers shown. LC/MS (Method F), MH+=999, rt=1.88 min.

Biological Test Methods

Fluorescence Anisotropy Binding Assay

The binding of the compounds of formula (I) to Bromodomain BRD2, BRD3 and BRD4 may be assessed using a Fluorescence Anisotropy Binding Assay.

The Bromodomain protein, fluorescent ligand (Reference compound K see above) and a variable concentration of test compound are incubated together to reach thermodynamic equilibrium under conditions such that in the absence of test compound the fluorescent ligand is significantly (>50%) bound and in the presence of a sufficient concentration of a potent inhibitor the anisotropy of the unbound fluorescent ligand is measurably different from the bound value.

All data was normalized to the mean of 16 high and 16 low control wells on each plate. A four parameter curve fit of the following form was then applied:

$$y=a+((b-a)/(1+(10^\wedge x/10^\wedge c)^\wedge d)$$

Where 'a' is the minimum, 'b' is the Hill slope, 'c' is the $pIC_{50}$ and 'd' or is the maximum.

Recombinant Human Bromodomains (Bromodomain BRD2 (1-473), Bromodomain BRD3 (1-435) and Bromodomain BRD4 (1-477)) were expressed in *E. coli* cells (in pET15b vector) with a six-His tag at the N-terminal. The His-tagged Bromodomain was extracted from *E. coli* cells using 0.1 mg/ml lysozyme and sonication. The Bromodomain was then purified by affinity chromatography on a HisTRAP HP column, eluting with a linear 10-500 mM Imidazole gradient, over 20 Cv. Further purification was completed by Superdex 200 prep grade size exclusion column. Purified protein was stored at −80° C. in 20 mM HEPES pH 7.5 and 100 mM NaCl.

Protocol for Bromodomain BRD2:

All components were dissolved in buffer composition of 50 mM HEPES pH7.4, 150 mm NaCl and 0.5 mM CHAPS with final concentrations of Bromodomain 2, 75 nM, fluorescent ligand 5 nM. 10 μl of this reaction mixture was added using a micro multidrop to wells containing 100 nl of various concentrations of test compound or DMSO vehicle (1% final) in Greiner 384 well Black low volume microtitre plate and equilibrated in dark 60 mins at room temperature. Fluorescence anisotropy was read in Envision (λex=485 nm, λEM=530 nm; Dichroic −505 nM).

Protocol for Bromodomain BRD3:

All components were dissolved in buffer of composition 50 mM HEPES pH7.4, 150 mm NaCl and 0.5 mM CHAPS with final concentrations of Bromodomains 3 75 nM, fluorescent ligand 5 nM. 10 μl of this reaction mixture was added using a micro multidrop to wells containing 100 nl of various concentrations of test compound or DMSO vehicle (1% final) in Greiner 384 well Black low volume microtitre plate and equilibrated in dark 60 mins at room temperature. Fluorescence anisotropy was read in Envision (λex=485 nm, λEM=530 nm; Dichroic −505 nM).

Protocol for Bromodomain BRD4:

All components were dissolved in buffer of composition 50 mM HEPES pH7.4, 150 mm NaCl and 0.5 mM CHAPS with final concentrations of Bromodomain 4 75 nM, fluorescent ligand 5 nM. 10 μl of this reaction mixture was added using a micro multidrop to wells containing 100 nl of various concentrations of test compound or DMSO vehicle (1% final) in Greiner 384 well Black low volume microtitre plate and equilibrated in dark 60 mins at room temperature. Fluorescence anisotropy was read in Envision (λex=485 nm, λEM=530 nm; Dichroic −505 nM).

Example 1 was tested in one or more of the above assays and was found to have a pIC50≥6.5.

Time Resolved Fluorescence Resonance Enemy Transfer (TR-FRET) Assay

The binding of the compounds of formula (I) to Bromodomains BRD2, BRD3 and BRD4 was assessed using a time resolved fluorescent resonance energy transfer binding assay, that measures the binding of an acetylated histone peptide to the bromodomain protein.

The bromodomain protein, histone peptide and a variable concentration of test compound are incubated together to reach thermodynamic equilibrium. The assay is configured such that in the absence of test compound the bromodomain and peptide are significantly bound (~30%) and in the presence of a sufficient concentration of a potent inhibitor this interaction is disrupted leading to a measurable drop in fluorescent resonance energy transfer.

Histone Peptide:

H-Ser-Gly-Arg-Gly-Lys(Ac)-Gly-Gly-Lys(Ac)-

Gly-Leu-Gly-Lys(Ac)-Gly-Gly-Ala-Lys(Ac)-

Arg-His-Gly-Ser-Gly-Ser-Lys(Biotin)-OH. 3TFA

The protected peptide was assembled on a solid-phase synthesiser using preloaded Wang resin and utilising standard Fmoc synthesis protocols. The C-terminal lysine was protected by a hyper acid-labile group allowing for its selective removal at the end of the assembly and attachment of the biotin. The crude peptide was obtained after cleavage from the resin with a mixture of trifluoroacetic acid (TFA), triisopropylsilane and water (95:2.5:2.5) for 3 h at room temperature and was then purified using a C18 reverse-phase column utilising a 0.1% TFA-buffered water/acetonitrile gradient. The resulting fractions were analysed and fractions which were >95% pure by analytical HPLC and giving the correct mw (by MALDiTOF mass spectroscopy) were pooled and freeze dried. The final material was analysed by HPLC to confirm purity.

Protein Production:

Recombinant Human Bromodomains (BRD2 (1-473), BRD3 (1-435) and BRD4 (1-477)) were expressed in *E. coli* cells (in pET15b vector) with a six-His tag at the N-terminal. The His-tagged Bromodomain was extracted from *E. coli* cells using sonication and purified using a nickel sepharose 6FF column, the proteins were washed and then eluted with 50 mM Tris-Hcl pH8.0. 300 mM NaCl, 1 mM β-mercaptoethanol and 20 mM Imidazole. Further purification was performed by affinity chromatography on a HisTRAP HP column, eluting with a linear 0-500 mM sodium chloride gradient, over 20 column volumes. Final purification was completed by Superdex 200 prep grade size exclusion column. Purified protein was stored at −80 C in 20 mM HEPES pH 7.5 and 100 mM NaCl. Protein identity was confirmed by peptide mass fingerprinting and predicted molecular weight confirmed by mass spectrometry.

Protocol for Bromodomain BRD2, 3 and 4 Assays:

All assay components were dissolved in buffer composition of 50 mM HEPES pH7.4, 50 mM NaCl and 0.5 mM CHAPS. The final concentration of bromodomain proteins were 100 nM and the histone peptide was 300 nM, these components are premixed and allowed to equilibrate for 1 hour in the dark. 8 μl of this reaction mixture was added to all wells containing 50 nl of various concentrations of test compound or DMSO vehicle (0.5% final) in Greiner 384 well black low volume microtitre plates and incubated in dark for 60 mins at room temperature. 20 of detection mixture containing anti-6his XL665 labeled antibody and streptavidin labeled with europium cryptate was added to all wells and a further dark incubation of at least 30 mins was performed. Plates were then read on the Envision platereader, (λex=317 nm, donor λEM=615 nm; acceptor λEM=665 nm; Dichroic LANCE dual). Time resolved fluorescent intensity measurements were made at both emission wavelengths and the ratio of acceptor/donor was calculated and used for data analysis. All data was normalized to the mean of 16 high and 16 low control wells on each plate. A four parameter curve fit of the following form was then applied:

$$y=a+((b-a)/(1+(10^x/10^c)^d)$$

Where 'a' is the minimum, 'b' is the Hill slope, 'c' is the pIC50 and 'd' is the maximum.

Examples 2-8 were tested in each of the above assays and were found to have pIC50s in the range 6.5-7.2. Example 2 was found to have pIC50 in the range 6.9-7.2 in each of the above assays.

Measurement of LPS Induced IL-6 Secretion from Whole Blood

Activation of monocytic cells by agonists of toll-like receptors such as bacterial lipopolysaccharide (LPS) results in production of key inflammatory mediators including IL-6. Such pathways are widely considered to be central to the pathophysiology of a range of auto-immune and inflammatory disorders.

Compounds to be tested are diluted to give a range of appropriate concentrations of which 1 μl of the diluted stocks is added to a 96 well plate. Following addition of whole blood (130 μl) the plates are incubated at 37 degrees (5% CO2) for 30 min before the addition of 10 μl of 2.8 ug/ml LPS, diluted in complete RPMI 1640 (final concentration=200 ng/ml), to give a total volume of 140 ul per well. After further incubation for 24 hours at 37 degrees, 140 μl of PBS are added to each well. The plates are sealed, shaken for 10 minutes and then centrifuged (2500 rpm×10 min). 100 μl of the supernatant are removed and IL-6 levels assayed by immunoassay (typically by MesoScale Discovery technology) either immediately or following storage at −20 degrees. Concentration response curves for each compound was generated from the data and an $IC_{50}$ value was calculated Examples 1-8 were tested in the above assay and were found to have pIC50s in the range 6.0-6.9. Example 2 was found to have a pIC50 of 6.7 in the above assay.

In Vivo Mouse Endotoxemia Model

High doses of Endotoxin (bacterial lipopolysaccharide) administered to animals produce a profound shock syndrome including a strong inflammatory response, dysregulation of cardiovascular function, organ failure and ultimately mortality. This pattern of response is very similar to human sepsis and septic shock, where the body's response to a significant bacterial infection can be similarly life threatening.

To test the compounds for use in the invention groups of eight Balb/c male mice are given a lethal dose of 15 mg/kg LPS by intraperitoneal injection. Ninety minutes later, animals were dosed intravenously with vehicle (20% cyclodextrin 1% ethanol in apyrogen water) or compound (10 mg/kg). The survival of animals is monitored at 4 days.

Oncology Cell Growth Assay

Human cell lines (n=33 comprising 15 heme cell lines, 14 breast cell lines and 4 other cell lines) were cultured in RPMI-1640 containing 10% fetal bovine serum, 1000 viable cells per well were plated in 384-well black flat bottom polystyrene plates (Greiner #781086) in 48 μl of culture media. All plates were placed at 5% $CO_2$, 37° C. overnight. The following day one plate was harvested with CellTiter-Glo (CTG, Promega #G7573) for a time equal to 0 (T0) measurement and compound (20 point titration from 14.7 uM to 7 pM) was added to the remaining plates. The final concentration of DMSO in all wells was 0.15%. Cells were incubated for 72 hours or the indicated time and each plate was developed with CellTiter-Glo reagent using a volume equivalent to the cell culture volume in the wells. Plates were shaken for approximately 2 minutes and chemiluminescent signal was read on the Analyst GT (Molecular Devices) or EnVision Plate Reader (Perkin Elmer).

Results are expressed as a percent of the T0 and plotted against the compound concentration. The T0 value was normalized to 100% and represents the number of cells at time of compound addition and the concentration response data were fit with a 4 parameter curve fit using XLfit software (model 205). The concentration that inhibited cell growth by 50% ($gIC_{50}$) is the midpoint of the 'growth window' (between the T0 and DMSO control). The Ymin–T0 value is determined by subtracting the T0 value (100%) from the Ymin value (%) determined from the fit of the concentration response curve. Values from the wells with no cells were subtracted from all samples for background correction.

Measurement of HPV Infected Cells

The W12 cell clone #20850, derived from a low grade cervical carcinoma (Stanley et al., Int. J. Cancer. V. 43. p. 672-676. 1989), carries episomal HPV16 genomes, maintained at approximately 100 copies per cell. Epithelial cell line C33A, which is not infected with any HPV strain was used as a negative control cell to assess non-specific cytotoxicity.

W12 and C33A cells were cultured with the compound of Example 2 for 2 days and viable cell content monitored by assaying [ATP] at end of this period. Data was normalised to DMSO control treated cells on day 2.

The compound reduced W12 cell viability in a concentration dependent manner (mean pIC50 value of 7.09±0.14, n=4) (with limited effect on C33A negative control cells). Viability at the maximal tested concentration (3 μM) was 34.8% and 73.5% in W12 and C33A cells respectively. These data show a specific effect on the virally infected cells and therefore that compounds of the invention may have utility in the treatment of HPV infected epithelial cells.

All publications, including but not limited to patents and patent applications, cited in this specification are herein incorporated by reference as if each individual publication were specifically and individually indicated to be incorporated by reference herein as though fully set forth.

What is claimed is:
1. A compound selected from the group consisting of
1-methylethyl ((2S,4R)-1-acetyl-2-methyl-6-{1-[2-(methyloxy)ethyl]-1H-pyrazol-4-yl}-1,2,3,4-tetrahydro-4-quinolinyl)carbamate;
6-(((2S,4R)-1-acetyl-6-(1-(2-methoxyethyl)-1H-1,2,3-triazol-4-yl)-2-methyl-1,2,3,4-tetrahydroquinolin-4-yl) amino)nicotinonitrile;
6-(((2S,4R)-1-acetyl-6-(2-(2-methoxyethyl)-2H-1,2,3-triazol-4-yl)-2-methyl-1,2,3,4-tetrahydroquinolin-4-yl) amino)nicotinonitrile;
1-((2S,4R)-4-((5-chloropyridin-2-yl)amino)-6-(1-(2-methoxyethyl)-1H-pyrazol-4-yl)-2-methyl-3,4-dihydroquinolin-1(2H)-yl)ethanone;
1-((2S,4R)-6-(1-(2-methoxyethyl)-1H-pyrazol-4-yl)-2-methyl-4-((5-methylpyridin-2-yl)amino)-3,4-dihydroquinolin-1(2H)-yl)ethanone;

1-((2S,4R)-4-((3-chlorophenyl)amino)-6-(1-(2-methoxyethyl)-1H-pyrazol-4-yl)-2-methyl-3,4-dihydroquinolin-1(2H)-yl)ethanone;

1-((2S,4R)-6-(1-(2-methoxyethyl)-1H-pyrazol-4-yl)-2-methyl-4-((5-methylpyrazin-2-yl)amino)-3,4-dihydroquinolin-1(2H)-yl)ethanone;

6-(((2S,4R)-1-acetyl-6-(1-(2-methoxyethyl)-1H-pyrazol-4-yl)-2-methyl-1,2,3,4-tetrahydroquinolin-4-yl)amino)nicotinonitrile; and salts thereof.

2. A compound which is 6-(((2S,4R)-1-acetyl-6-(1-(2-methoxyethyl)-1H-pyrazol-4-yl)-2-methyl-1,2,3,4-tetrahydroquinolin-4-yl)amino)nicotinonitrile or a salt thereof.

3. A compound according to claim 1 or a pharmaceutically acceptable salt thereof.

4. A pharmaceutical composition which comprises a compound or a pharmaceutically acceptable salt thereof as defined in claim 3 and one or more pharmaceutically acceptable carriers, diluents or excipients.

5. A combination pharmaceutical product comprising a compound or a pharmaceutically acceptable salt thereof as defined in claim 3 together with one or more other therapeutically active agents.

6. A method of treating diseases or conditions mediated by BET family bromodomain proteins in a subject in need thereof which comprises administering a therapeutically effective amount of compound or a pharmaceutically acceptable salt thereof as defined in claim 3.

7. A method of treatment according to claim 6, wherein the disease or condition is a chronic autoimmune and/or inflammatory condition.

8. A method of treatment according to claim 6, wherein the disease or condition is cancer.

* * * * *